United States Patent [19]

Yasukawa et al.

[11] Patent Number: 5,795,301
[45] Date of Patent: Aug. 18, 1998

[54] DISPLAY METHOD USED IN PORTABLE PULSE MEASURING DEVICE

[75] Inventors: Naoaki Yasukawa, Suwa; Chiaki Nakamura, Chiba, both of Japan

[73] Assignees: Seiko Epson Corporation, Tokyo; Seiko Instruments, Inc., Chiba, both of Japan

[21] Appl. No.: 692,938

[22] Filed: Aug. 6, 1996

[30] Foreign Application Priority Data

Aug. 31, 1995 [JP] Japan ............ 7-224319
Sep. 12, 1995 [JP] Japan ............ 7-234470
Sep. 12, 1995 [JP] Japan ............ 7-234472

[51] Int. Cl.⁶ .................................. A61B 5/02
[52] U.S. Cl. ............ 600/500; 600/502; 600/503; 482/8
[58] Field of Search ............ 128/898, 687, 128/688, 689, 690, 696; 482/3, 6, 7, 8, 9, 4, 900, 901; 600/500, 501, 502, 503, 504

[56] References Cited

U.S. PATENT DOCUMENTS 5,475,725  12/1995  Nakamura ............ 128/689

*Primary Examiner*—John P. Lacyk
*Assistant Examiner*—Rosiland Kearney
*Attorney, Agent, or Firm*—Eric B. Janofsky

[57] ABSTRACT

For the purpose of realizing a display method for a portable electronic measuring device that allows the user to know his condition more easily and in greater detail by making it easy for him to read the display of measured results even if the display device is limited in size due to its portability, a bar graph is displayed in dot display area (134) of liquid crystal display device (13) of the portable pulse measuring device which extends up at each time interval according to the absolute value of the pulse rate after the measurement of time is started and until the pulse rate reaches a prescribed range, and after the pulse rate reaches the prescribed range, a bar graph is displayed that extends in the positive direction or the negative direction at each time interval according to the difference from the prescribed reference pulse rate. When temporal changes in the pitch during running are displayed in dot display area (134), they are displayed in a segmented graph.

18 Claims, 21 Drawing Sheets

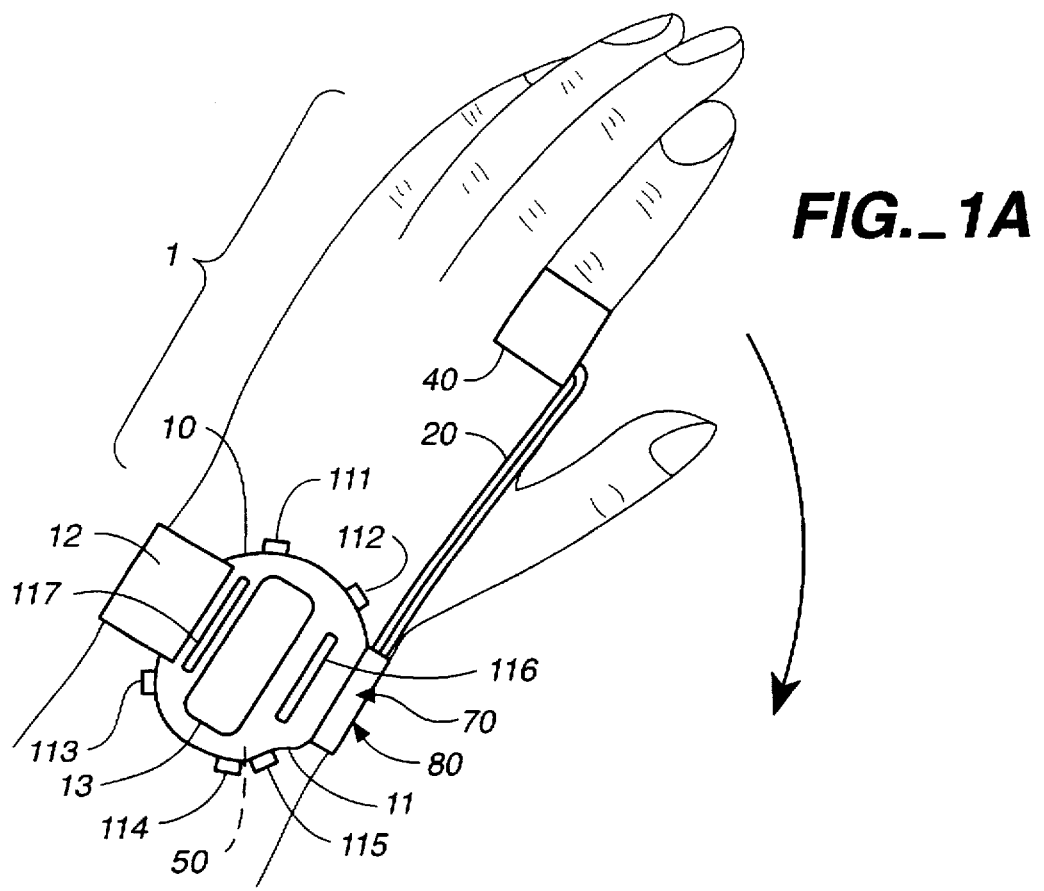
FIG._1A
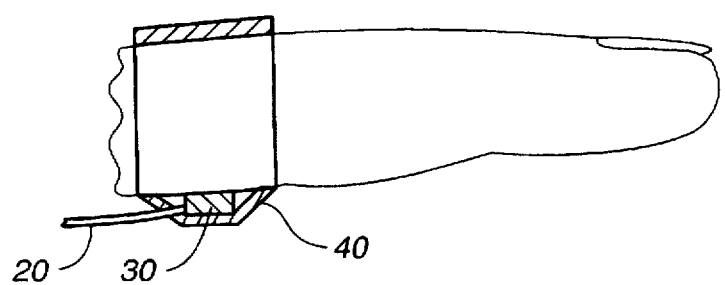
FIG._1B

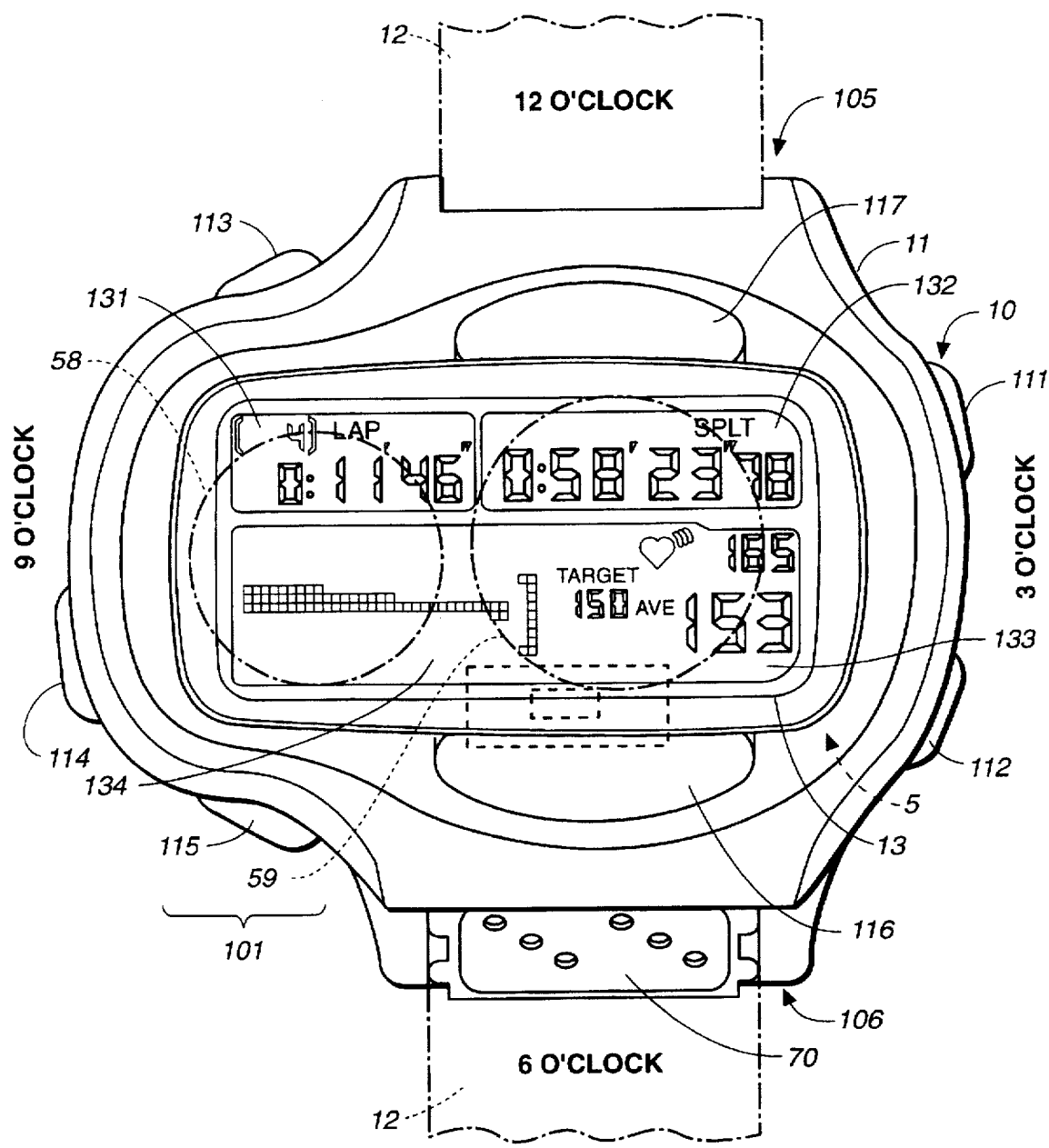
FIG._2

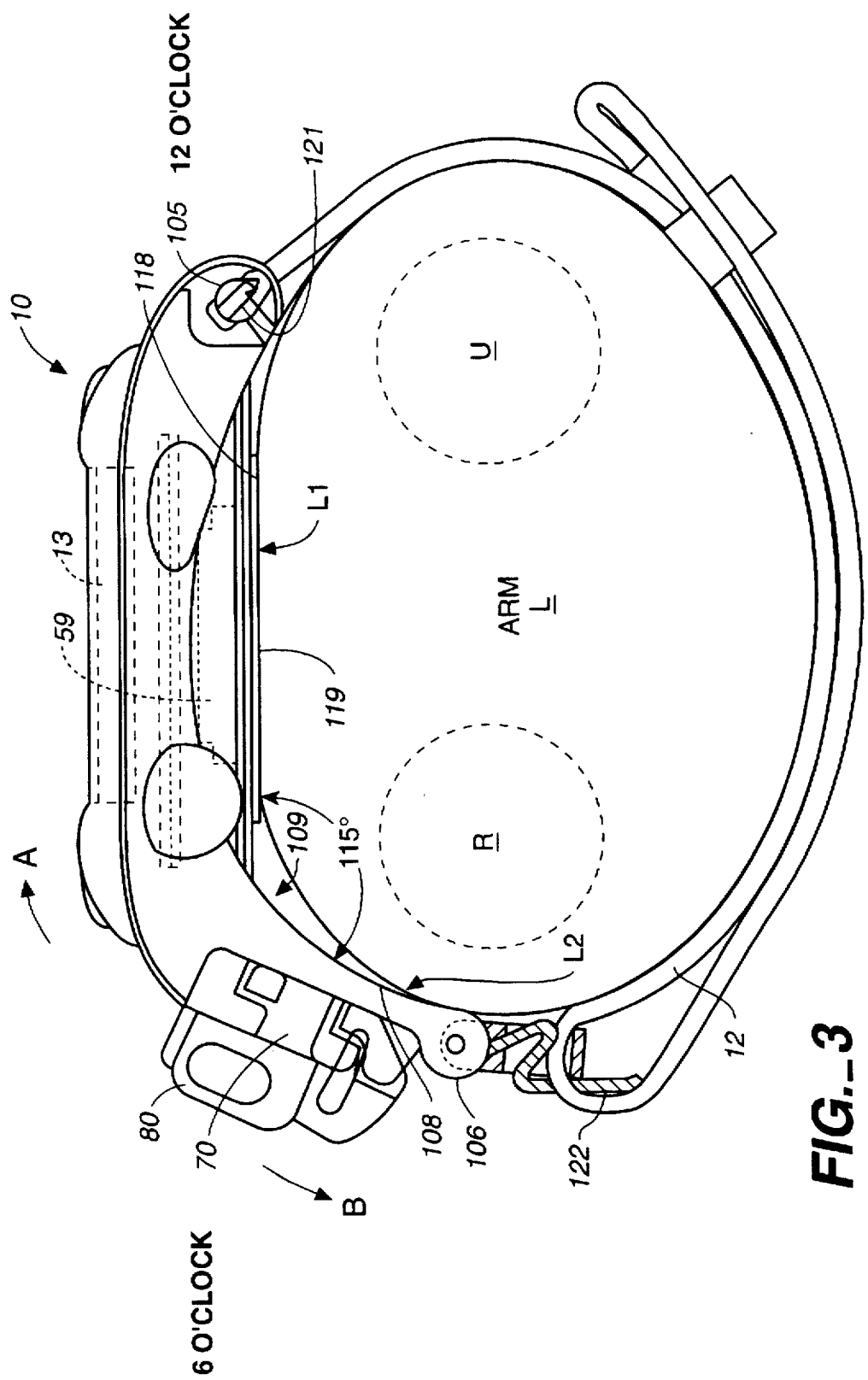
FIG._3

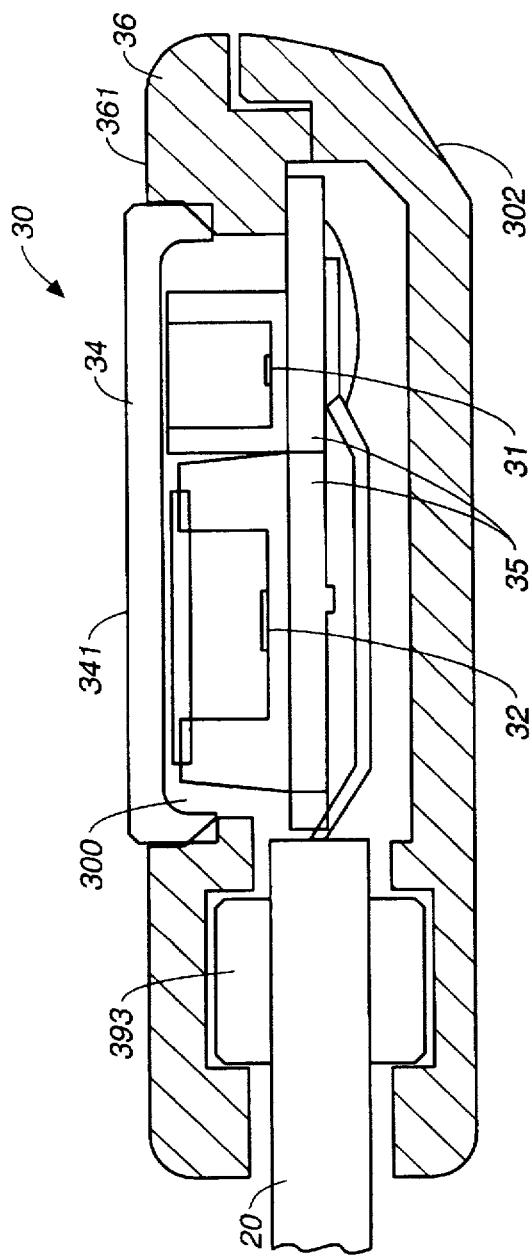
*FIG._4*
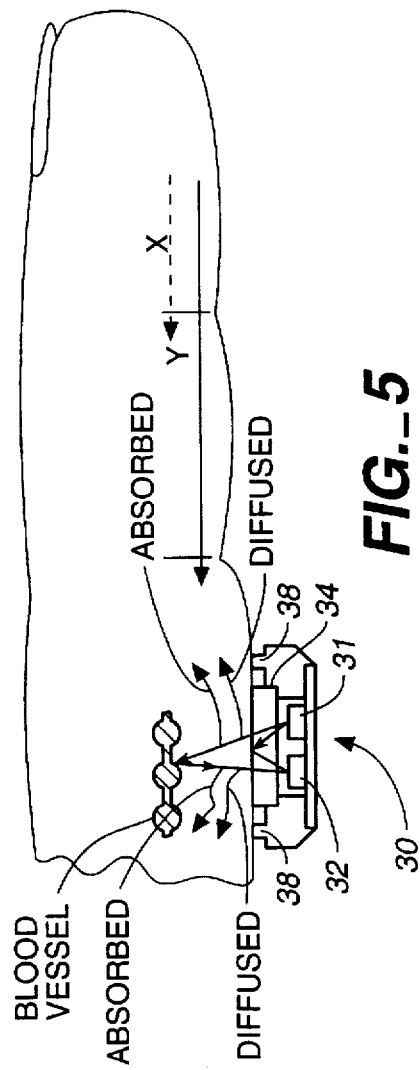
*FIG._5*

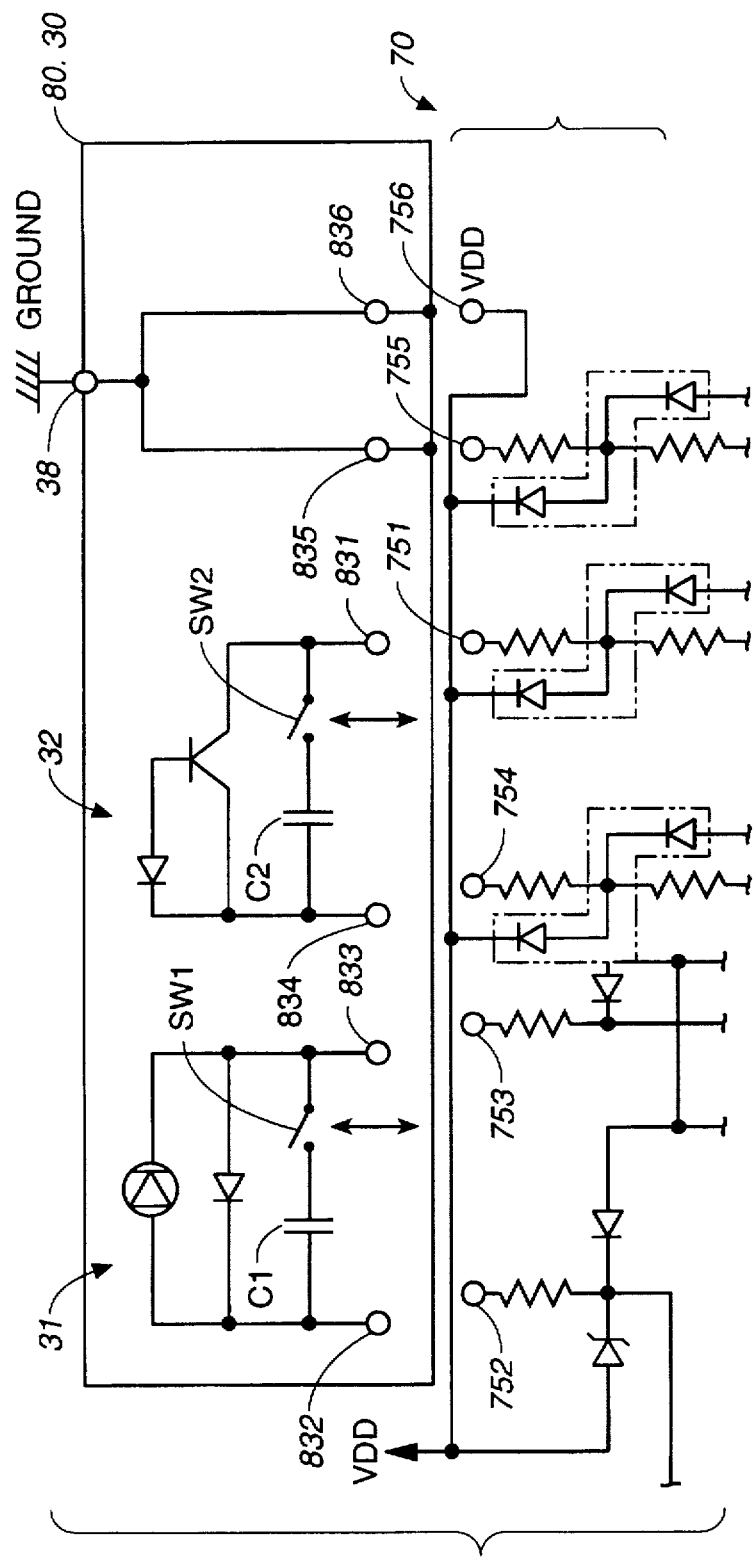
FIG._6

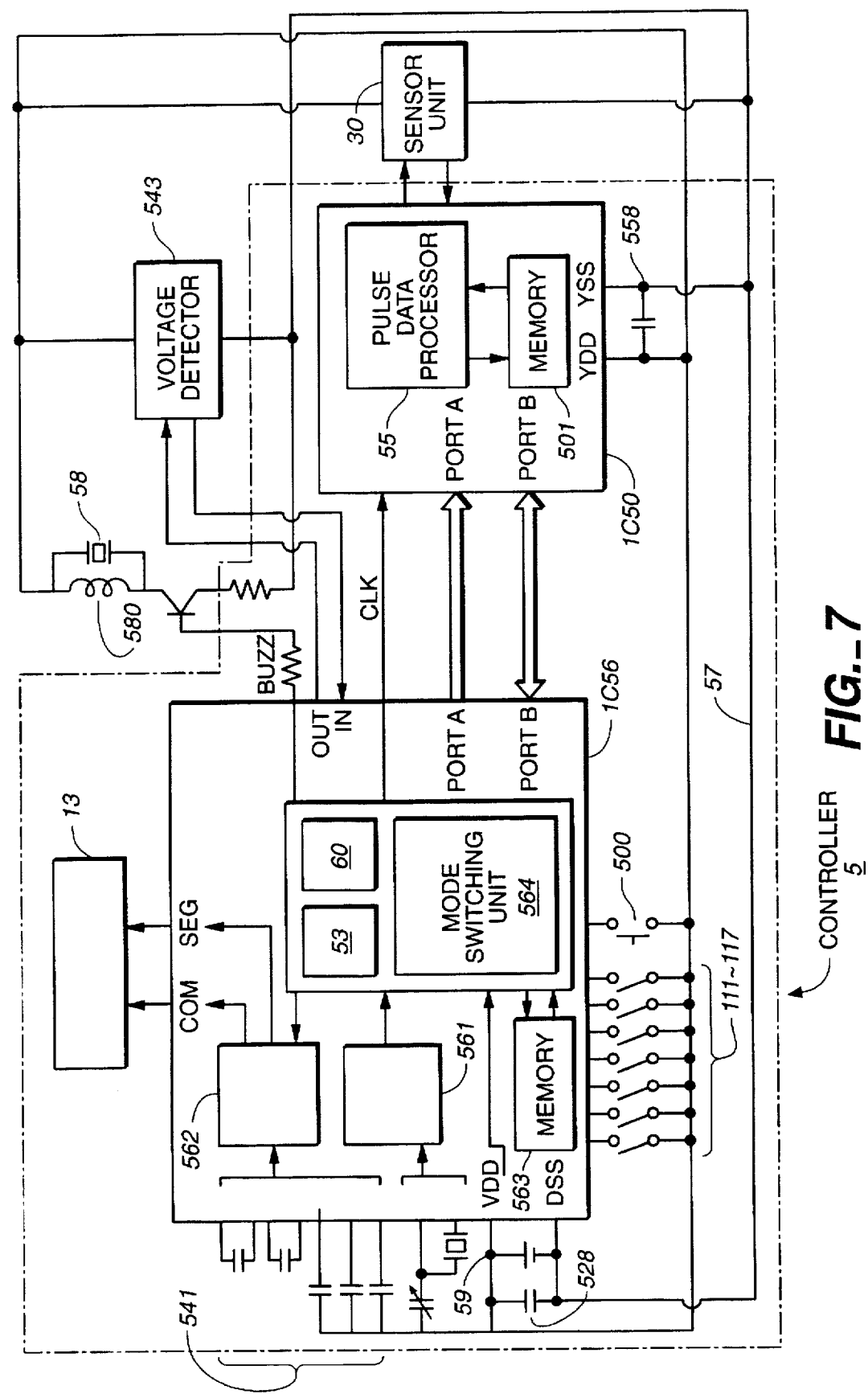
FIG._7

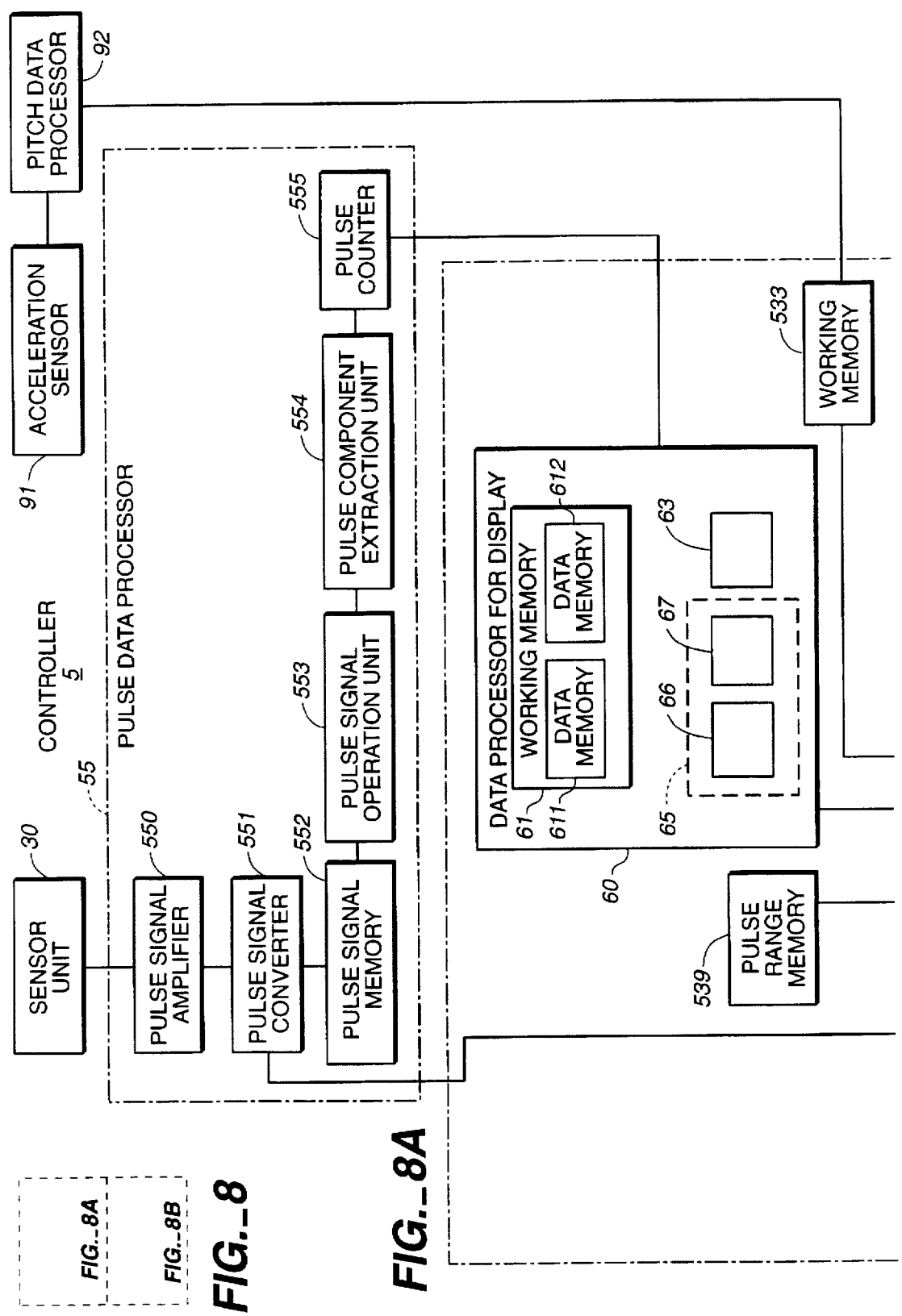

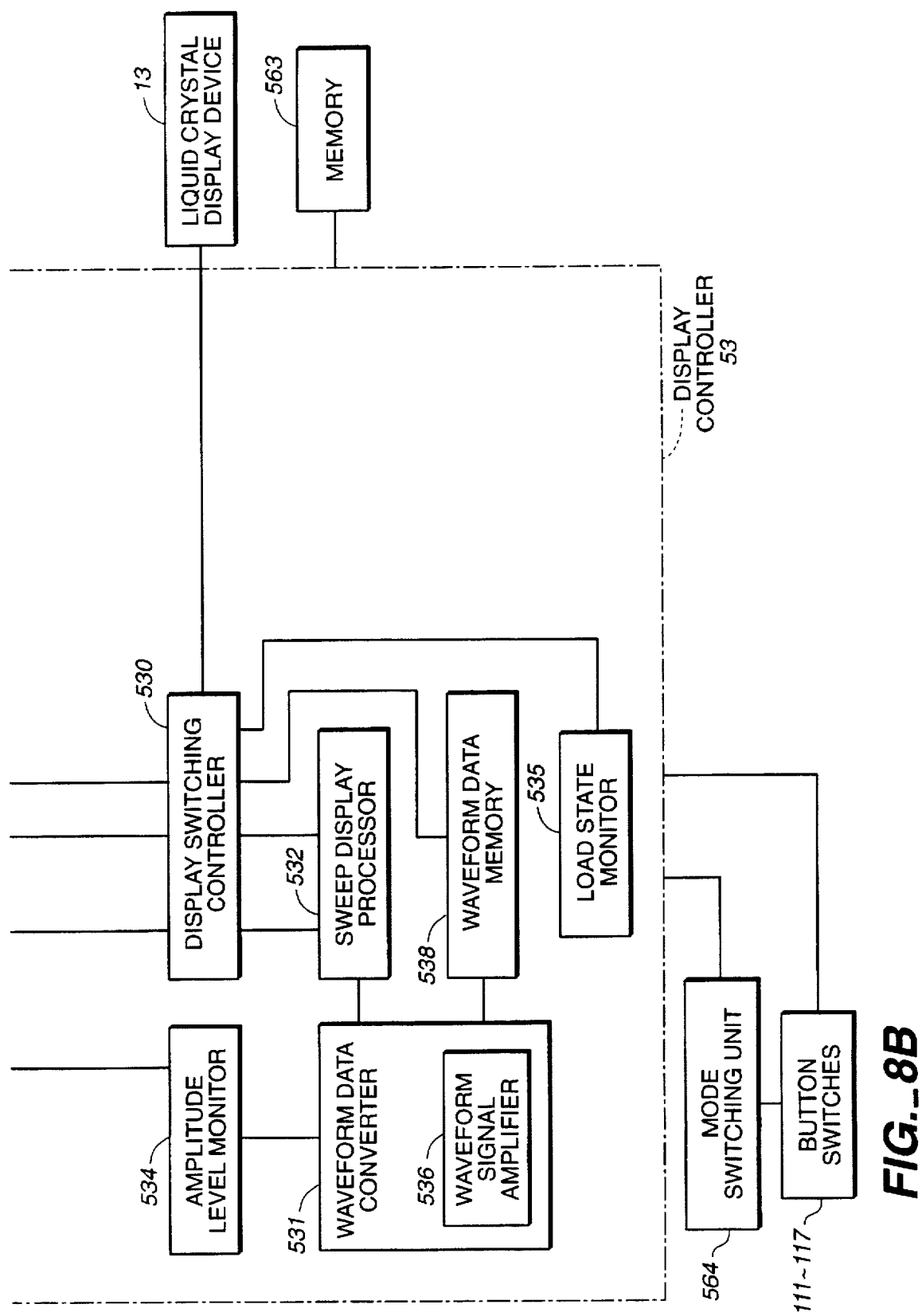
FIG._8B

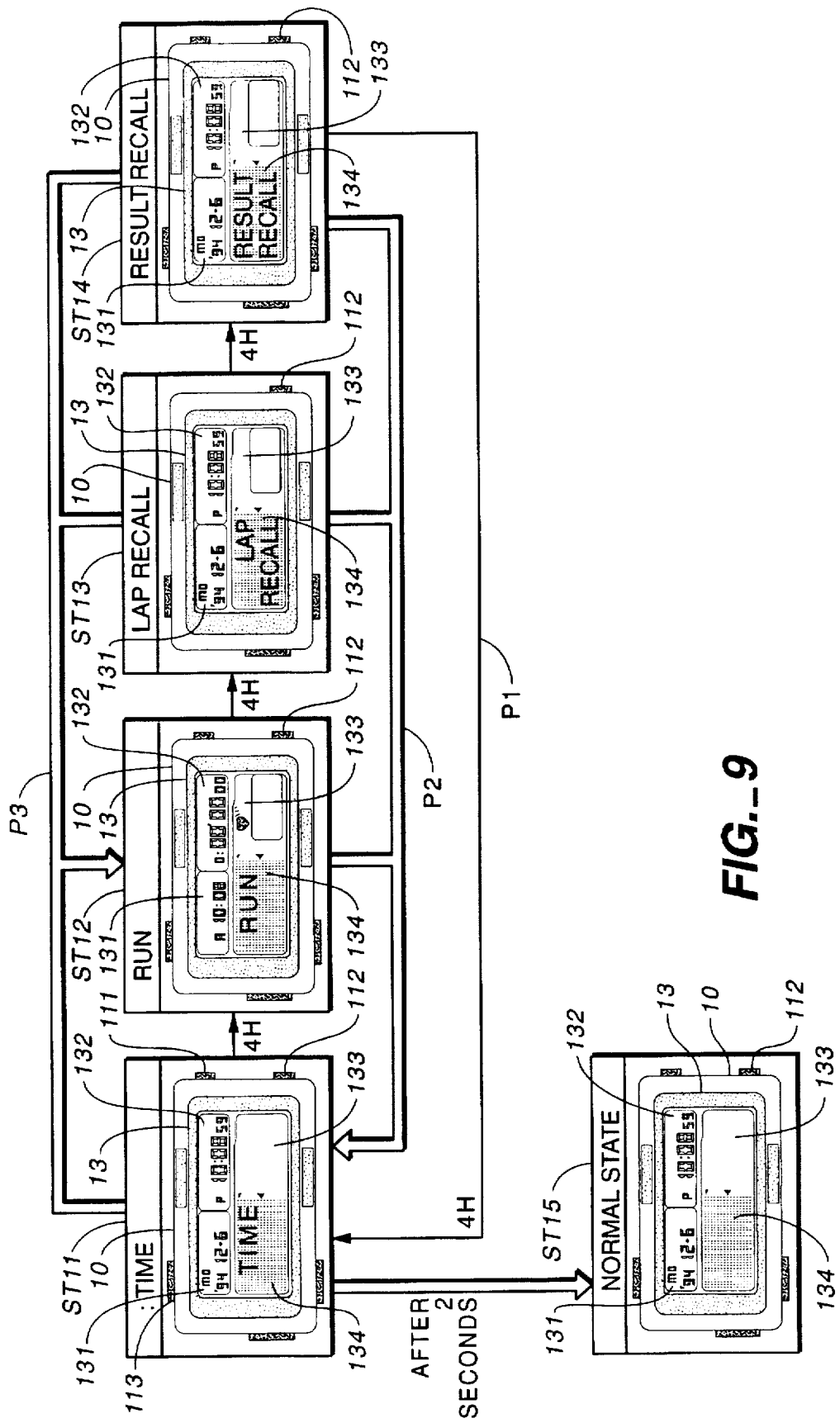
FIG._9

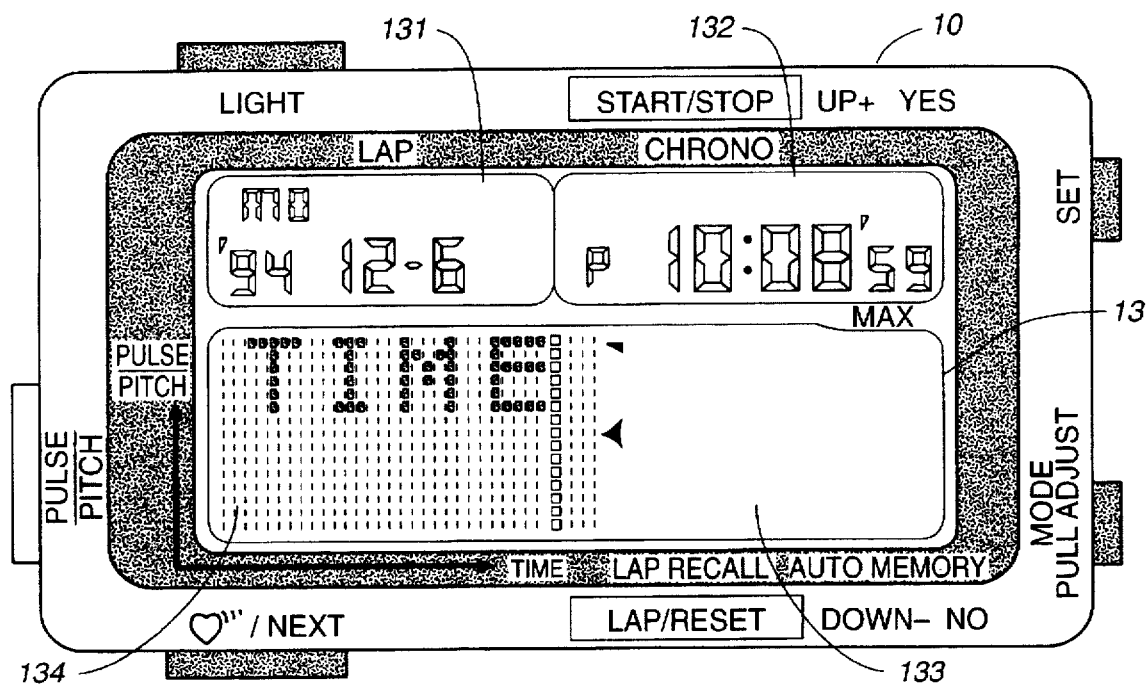
FIG._10
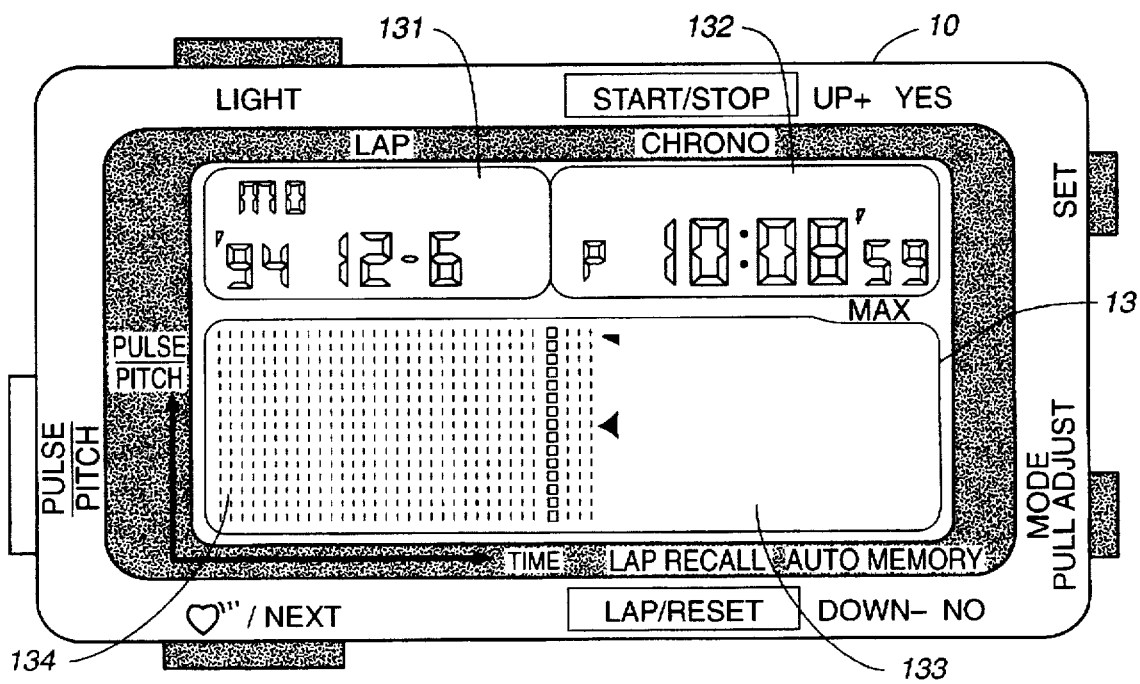
FIG._11

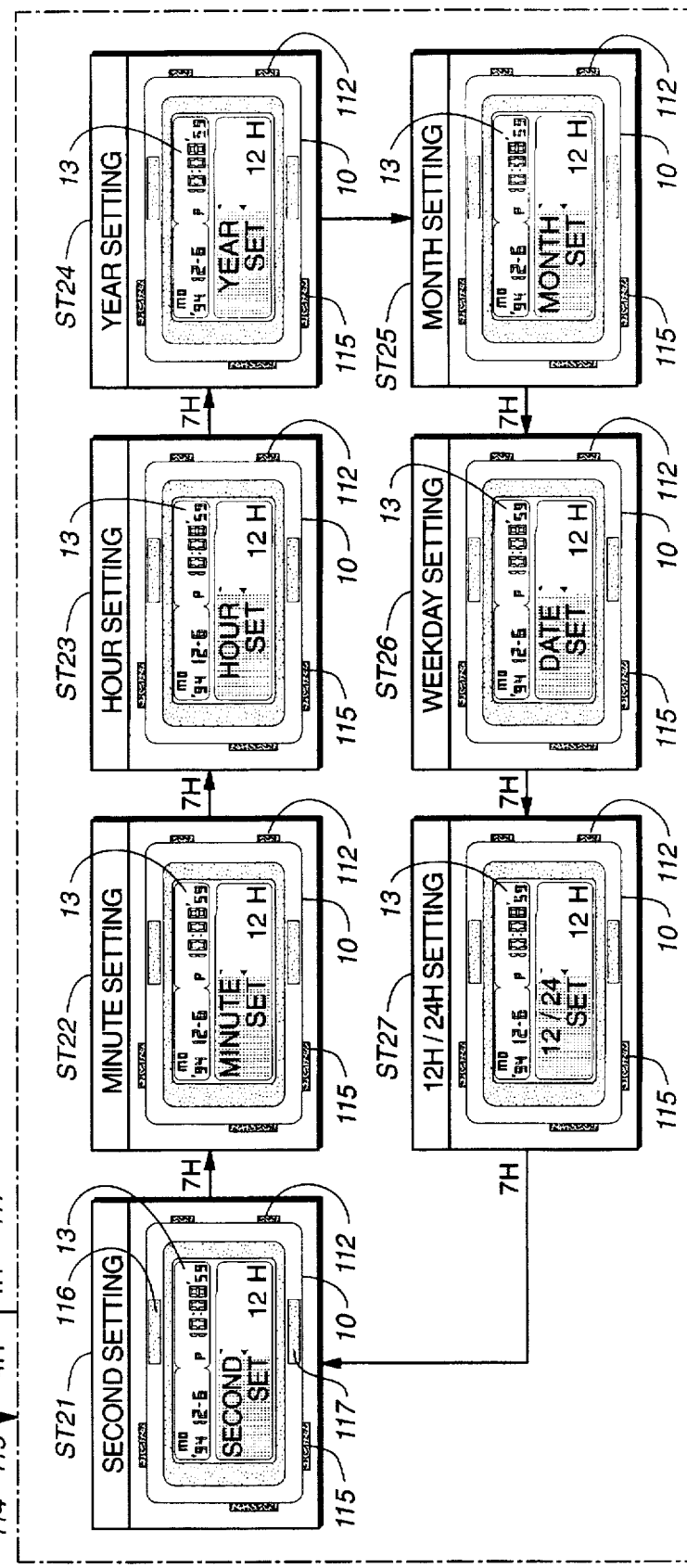
FIG._12

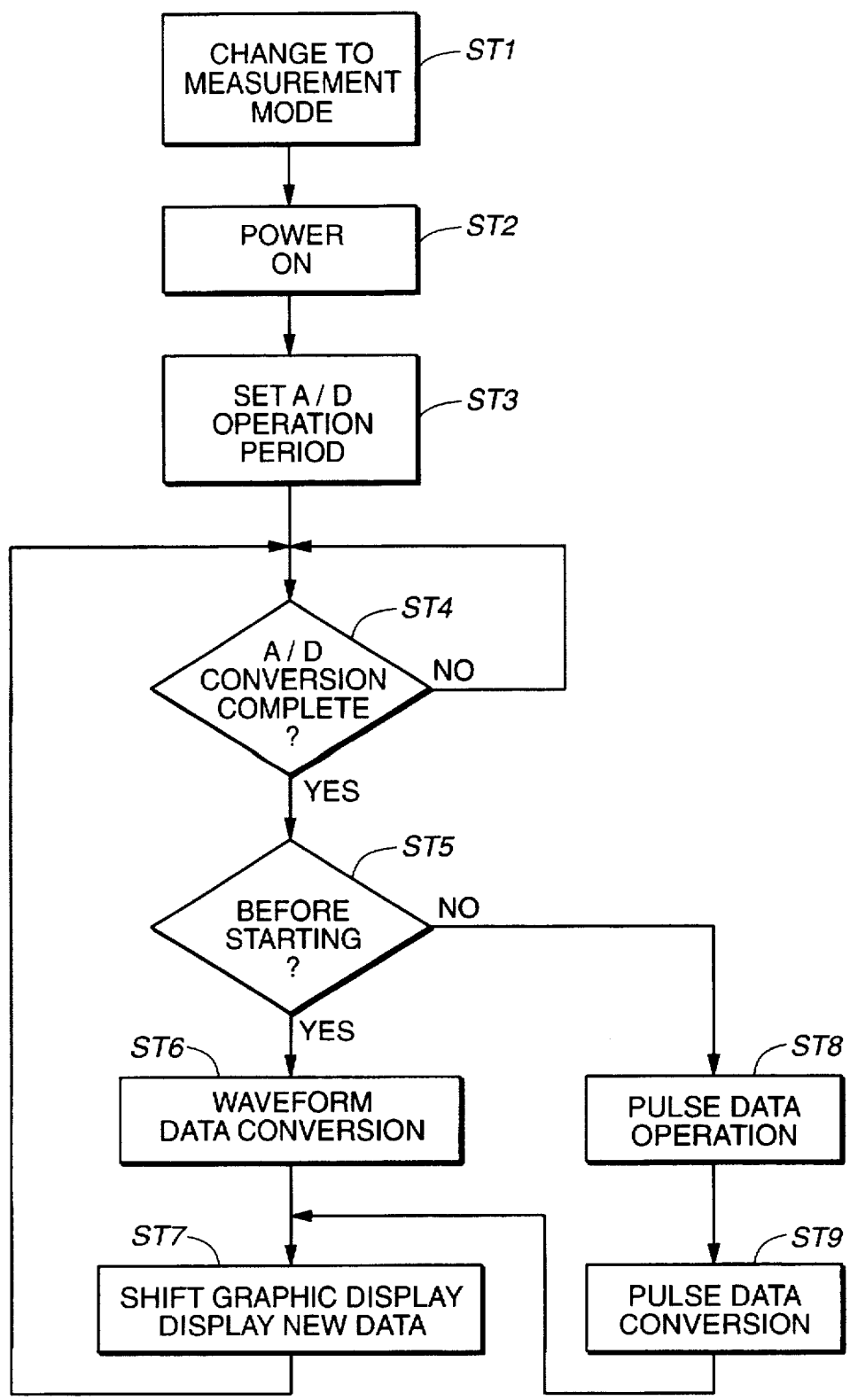
FIG._13

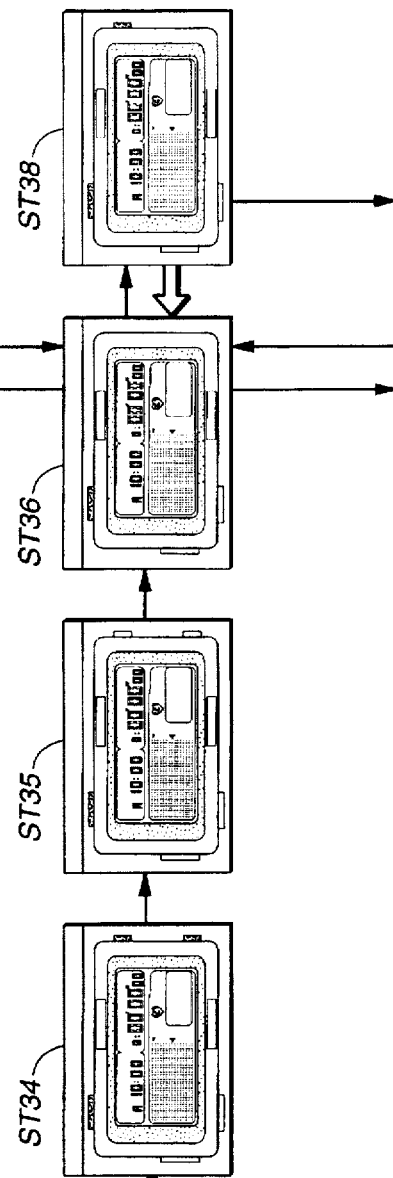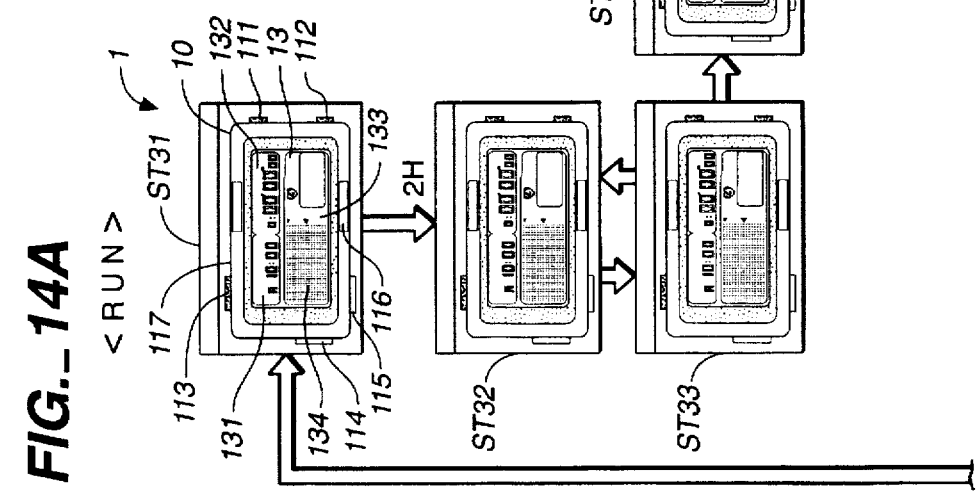
FIG._14A
FIG._14

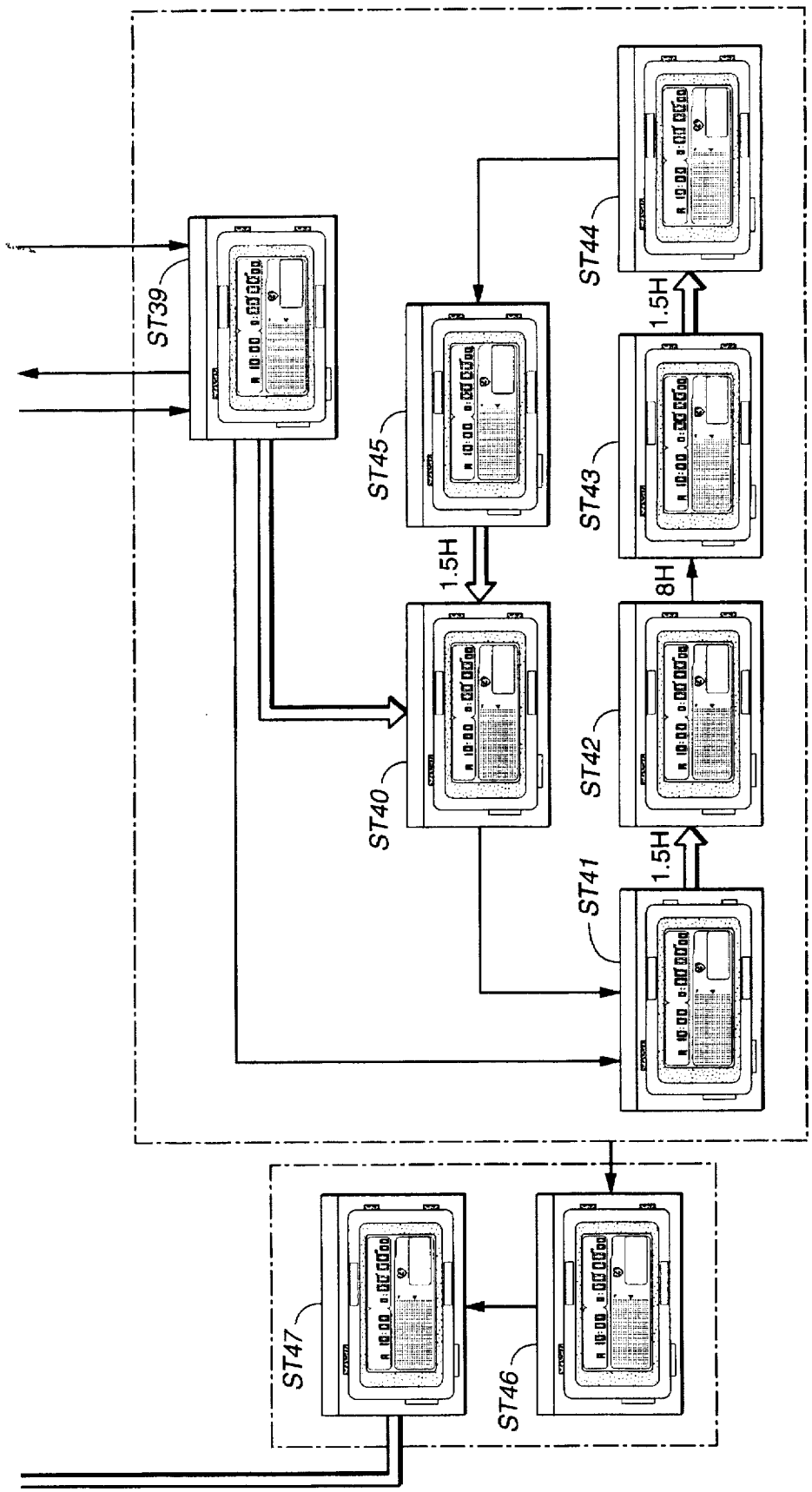
FIG._14B

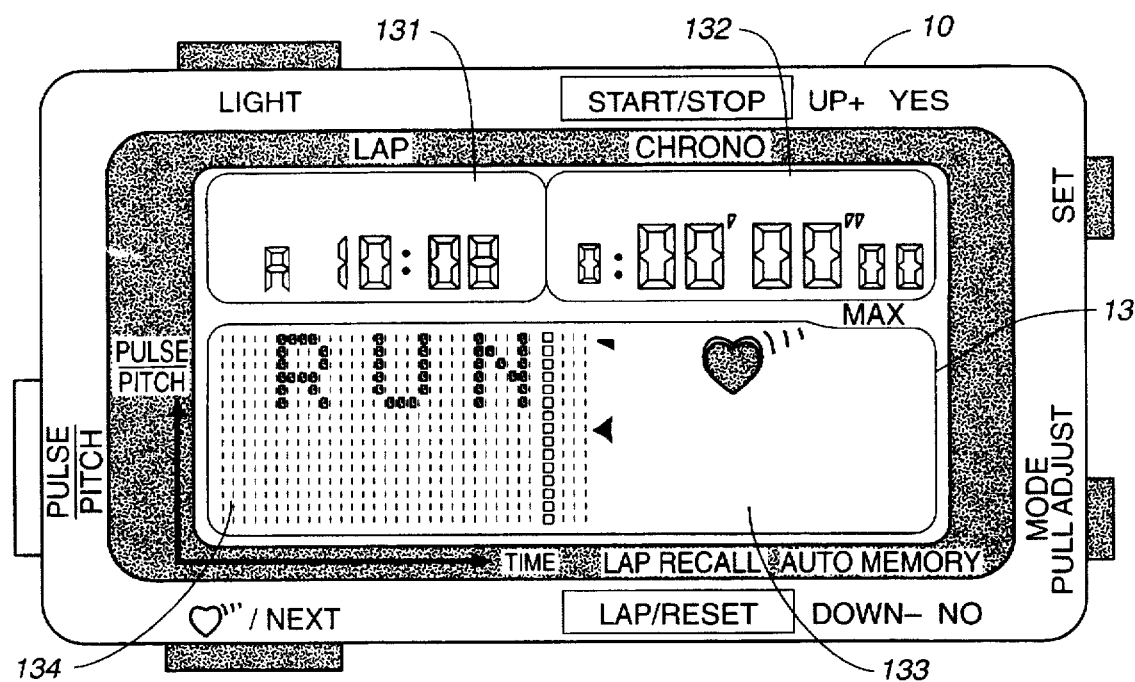
FIG._15
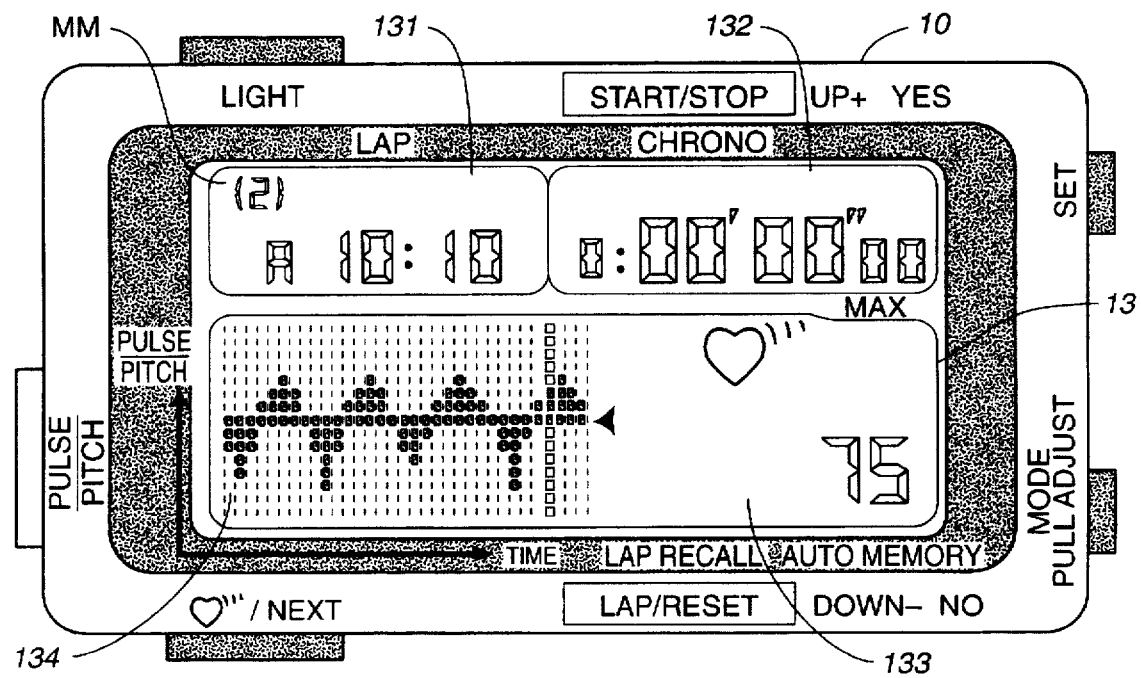
FIG._16

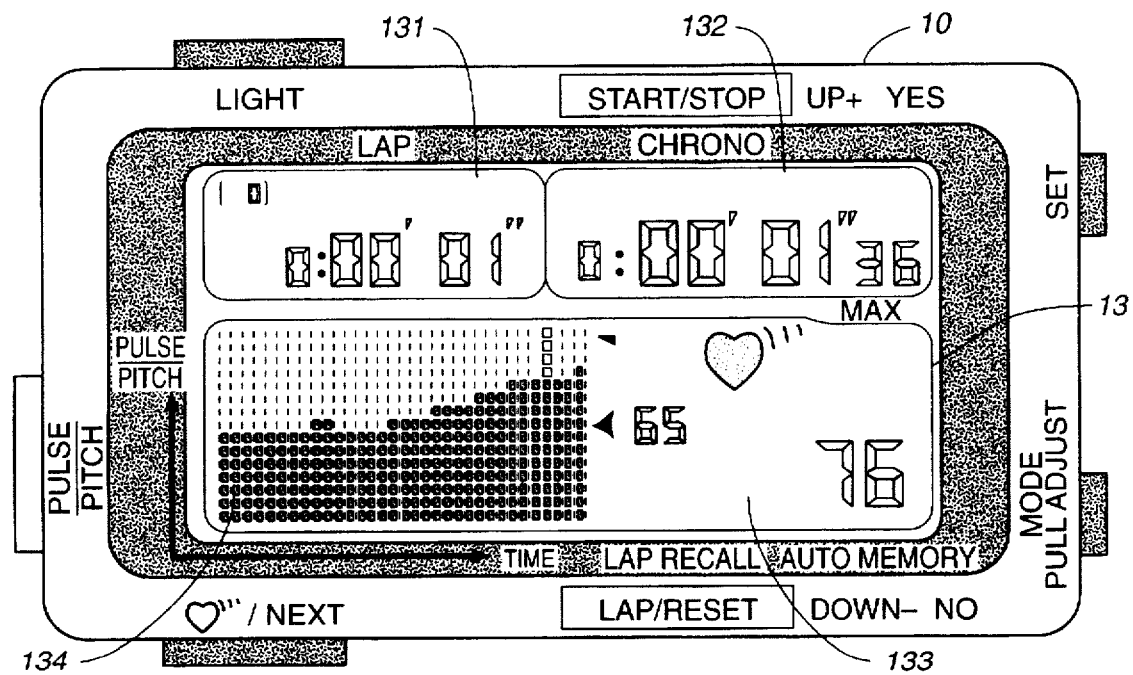
FIG._17
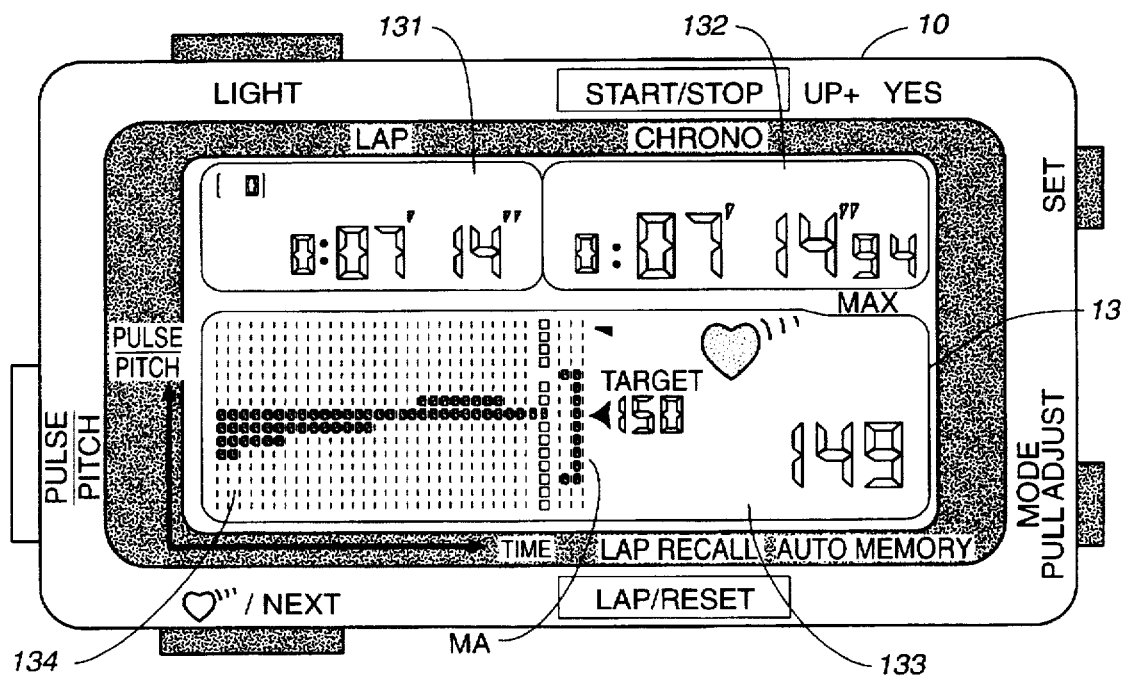
FIG._18

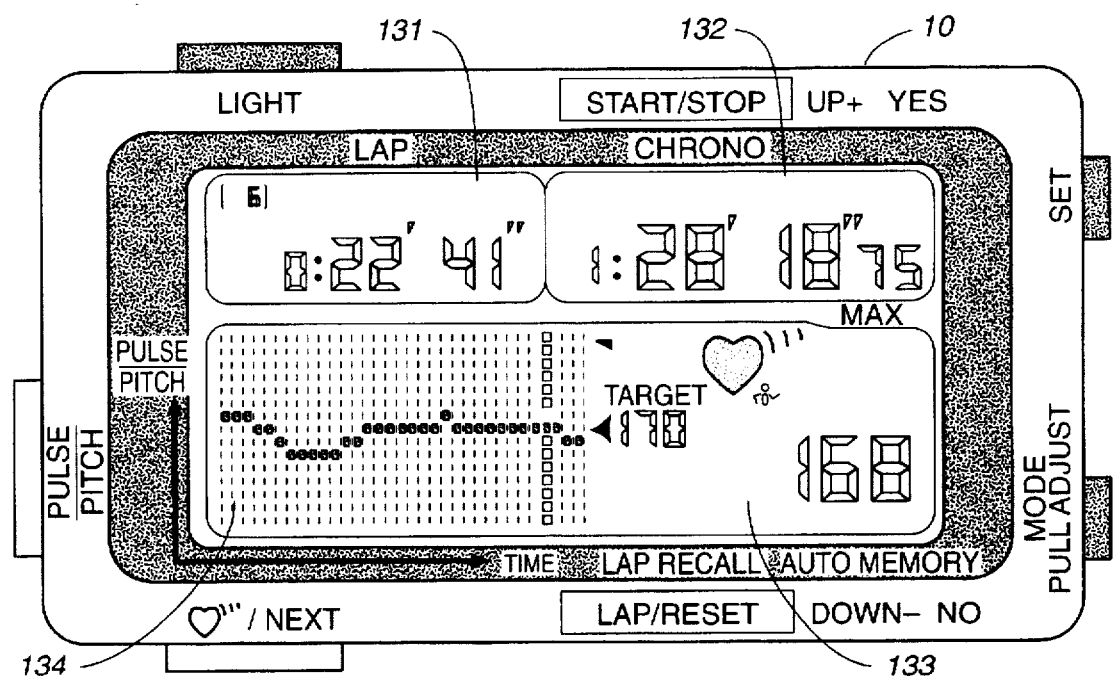
FIG._19
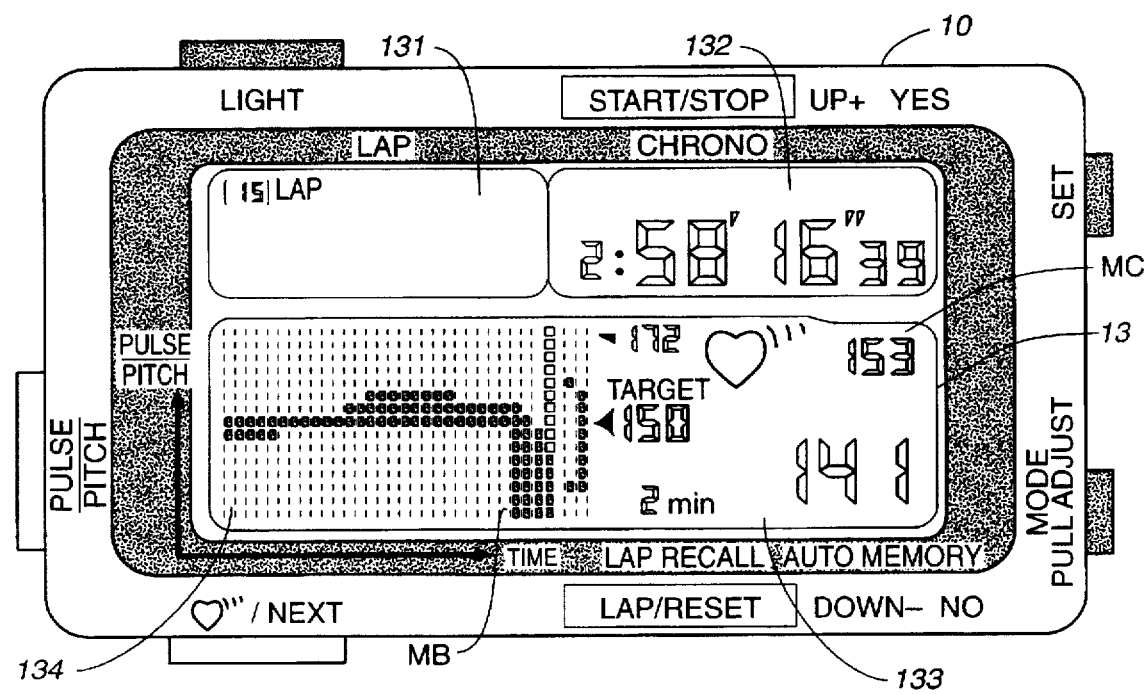
FIG._20

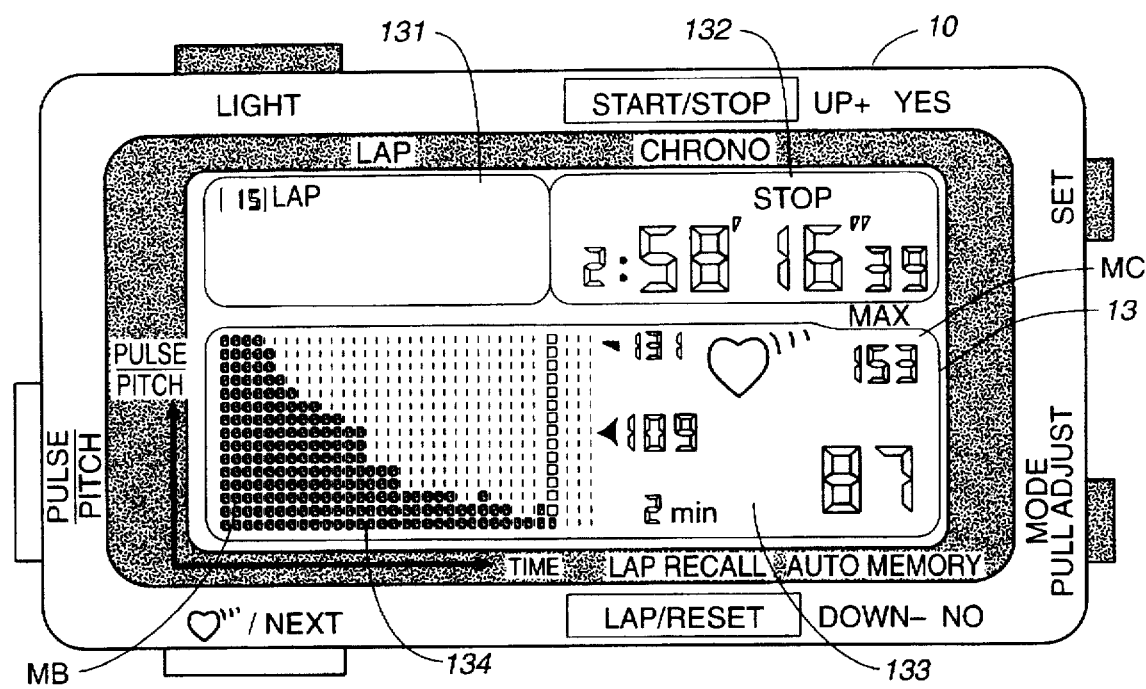
FIG._21
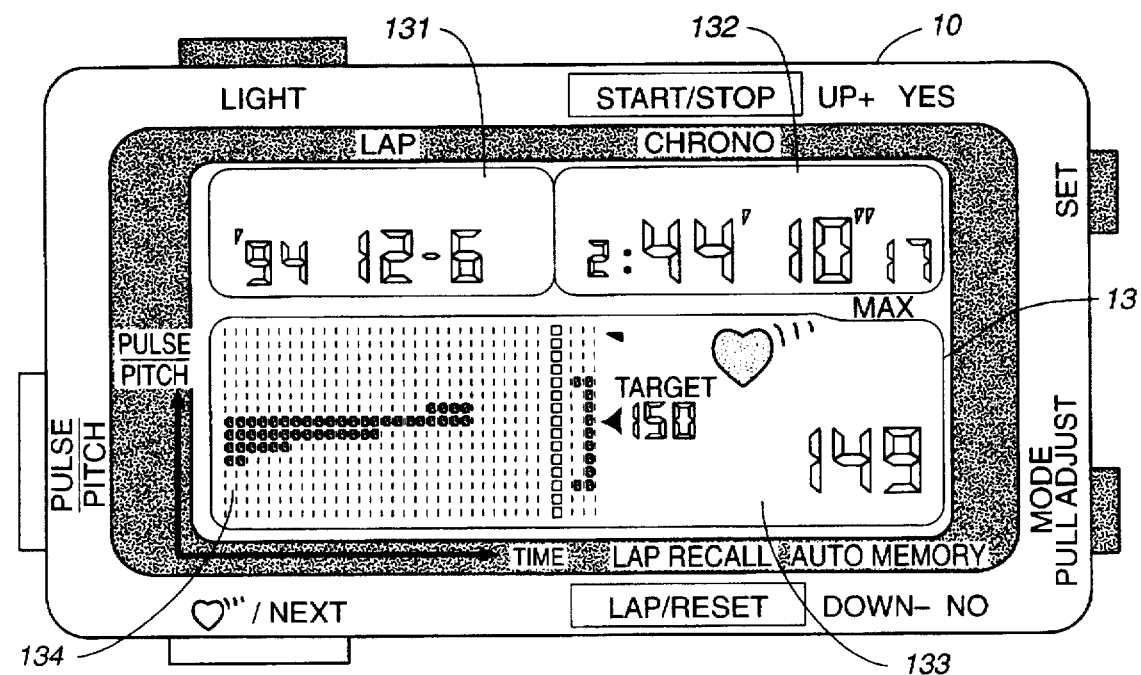
FIG._24

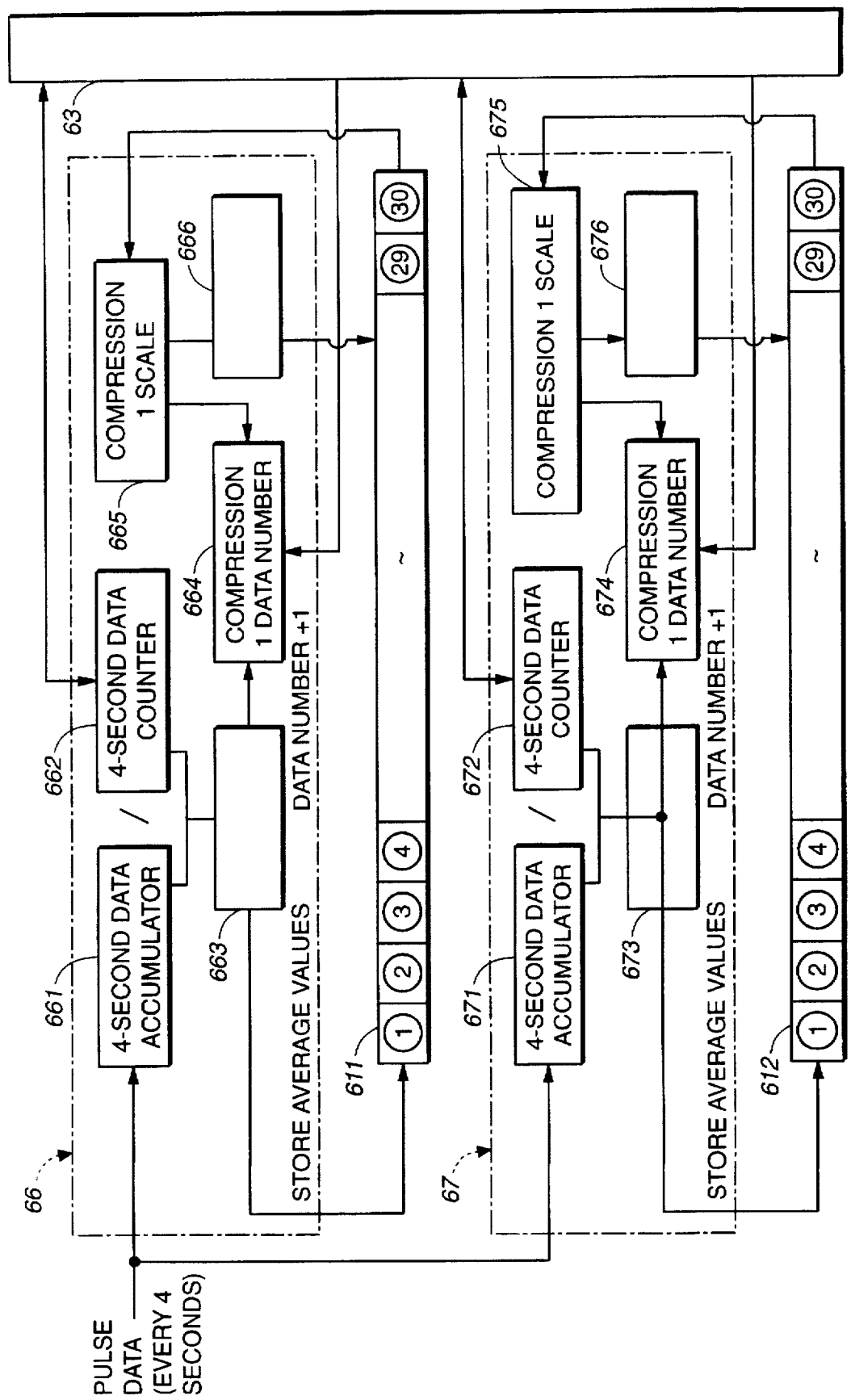
FIG._22

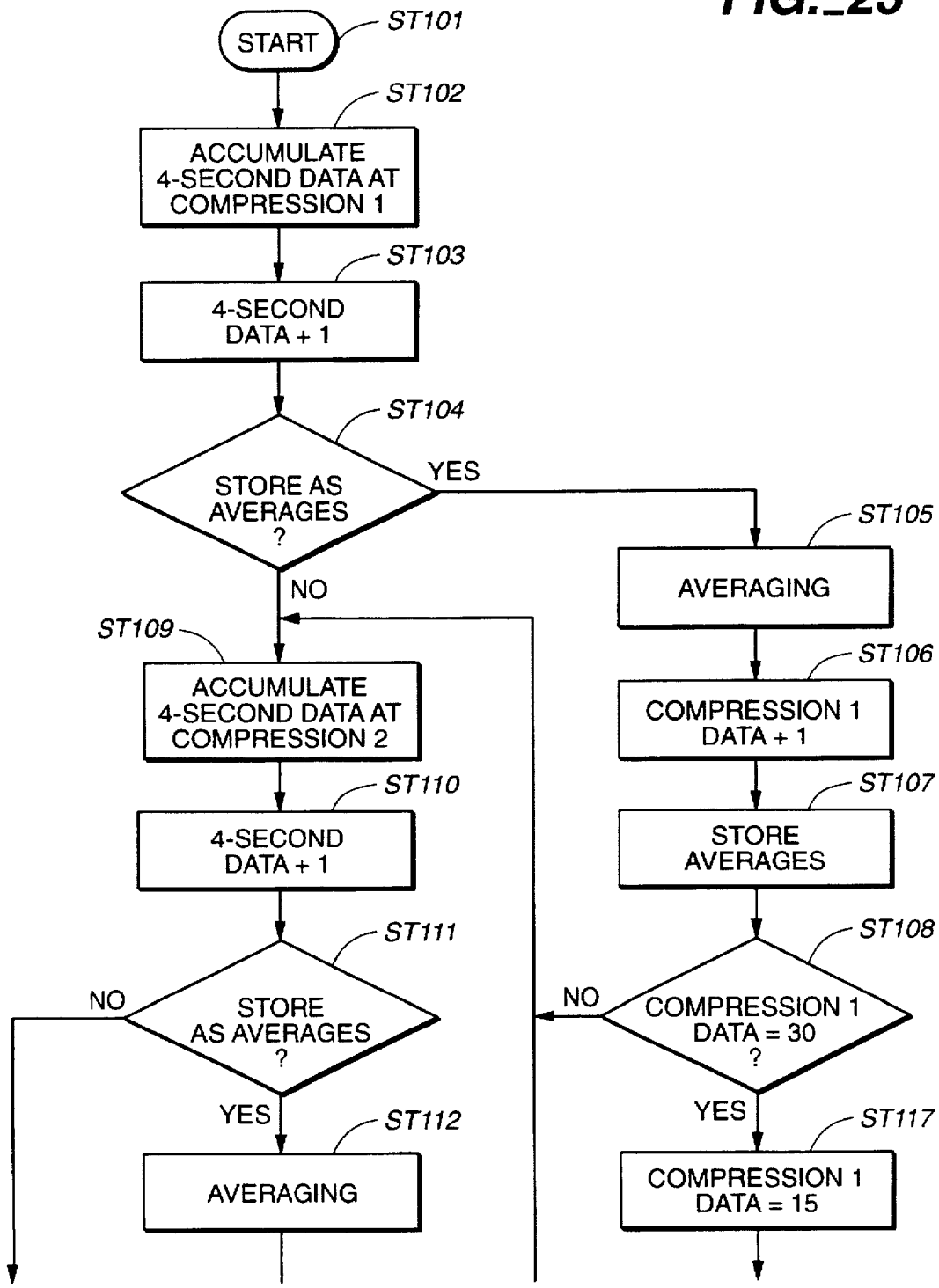

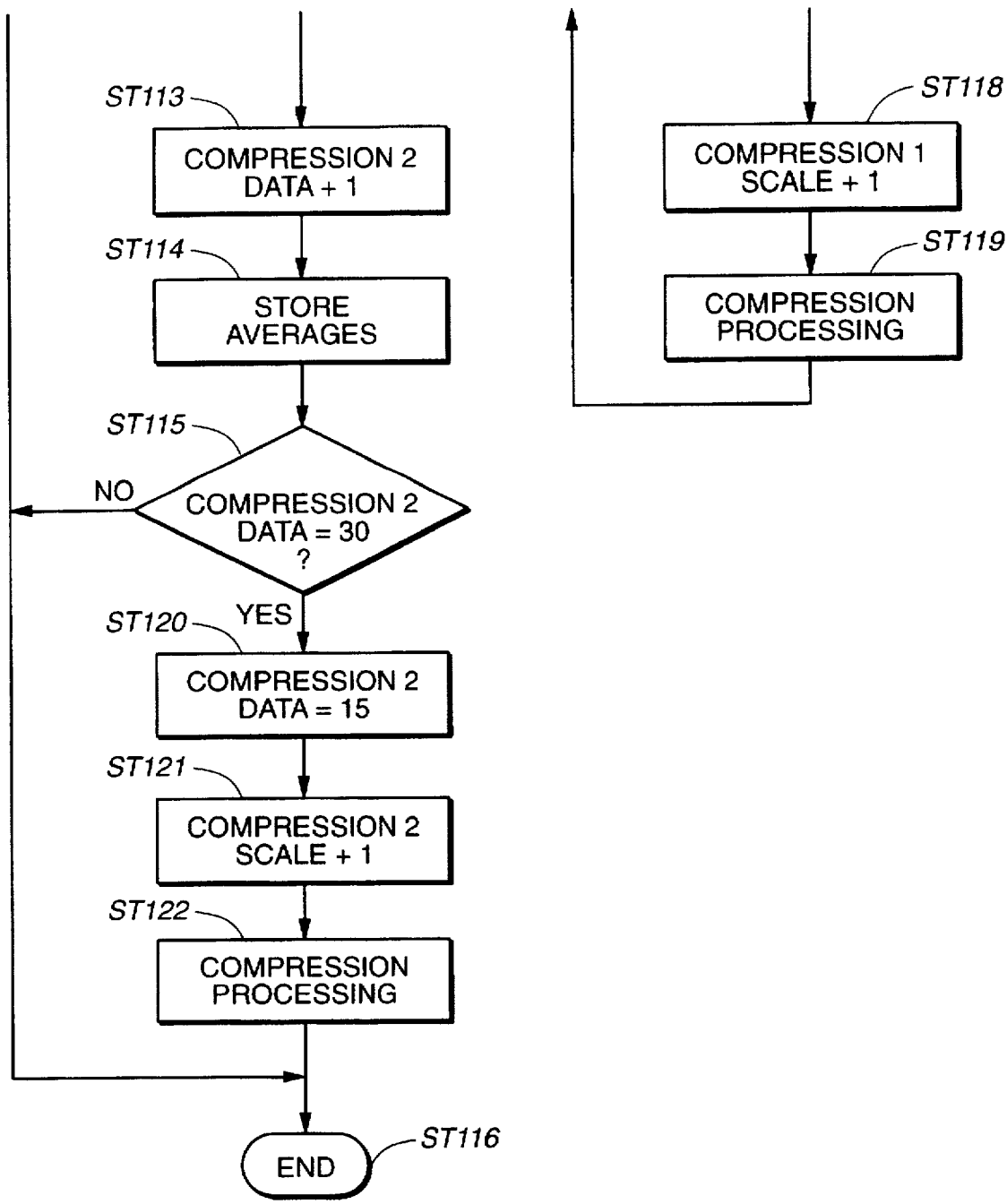
FIG._23B

DISPLAY METHOD USED IN PORTABLE PULSE MEASURING DEVICE

BACKGROUND OF THE INVENTION

1. Field of the Invention

The present invention relates generally to a display method for data, in a portable pulse measuring device that displays the pulse rate, among other data. In particular, the present invention is directed to displaying data on a wrist-worn portable pulse measuring device.

2. Description of the Related Art

When a portable pulse measuring device capable of measuring pulse rate and other pulse information while being worn on a wrist has a built-in watch function as well, it can be used as a portable pulse measuring device that measures and displays both the pulse rate and lap time while running. In configuring this kind of portable pulse measuring device, generally the current pulse rate and the time elapsed from the start time are displayed in segments on a liquid crystal display device.

However, in this kind of portable pulse measuring device, since a marathon runner can only occasionally view the display when running in a marathon, it is difficult to see any trend and the runner cannot fully grasp his physical condition because only the current pulse rate is displayed using segments.

If measurement of the pulse rate is started without noting that warm-up or preparation is not complete in the internal circuitry when measuring the pulse rate while running using this type of portable pulse measuring device, a user may fail to measure the pulse rate. This kind of failure is critical in that measurement of the pulse rate during a marathon cannot be redone. Therefore, a method can be considered that displays the pulse rate from before starting as long as preparation of the electronic circuitry, etc., is complete.

However, in this method, a user cannot confirm the reliability of measurement results before starting. That is, since the pulse rate is obtained from the frequency of the alternating current component of the pulse signal, even if the pulse detection unit is poorly attached, if there is an alternating current component in the pulse signal, a value is obtained as the pulse rate. Therefore, the state of the pulse detection unit cannot be confirmed to be good or bad merely by the display of the pulse rate.

In this type of portable pulse measuring device, the more functions that are provided, the more often mode selection will be performed, and each time information on the selected mode must be displayed in the display device. This mode information is continually displayed in the display device in conventional electronic devices so that the user can confirm at any time which mode is set.

However, in multifunction portable pulse measuring devices, even if there is much information that must be displayed, if a display area dedicated to displaying mode information is provided and the information is continually displayed there, then the area for displaying other information becomes unavoidably small. Since the area for information display must also be made small, it is difficult to read the displayed information. But if the display areas for both are expanded, a large display device would have to be used, thus detracting from the portability. Further, in a multifunction portable pulse measuring device, the more functions there are, the more power that is consumed as compared to a regular watch, but the power supply cannot be made larger because portability must be maintained. Therefore, in a method that continuously displays information on the selected mode as in the conventional device, battery life is that much shorter.

If the temporal changes in the pulse rate are to be displayed in this type of portable pulse measuring device while running, normally data measured over a period of time exceeding 2 hours must be displayed on a display device of limited size. Therefore, measured results are displayed sequentially on a time base set with a sufficient margin.

However, in this kind of display method, if used in a situation wherein the measurement time is short, then only a small amount of data will be displayed in a small area of the display device, thus making it difficult to use.

OBJECTS OF THE INVENTION

Therefore, it is an object of the present invention to overcome the aforementioned problems.

It is an additional object of the present invention to provide a portable electronic measuring device that allows the user to know his condition more easily and in greater detail by making it easy for him to read the display of measured results even if the display device is limited in size due to its portability.

It is a further object of the present invention to provide a portable pulse measuring device that makes it possible to confirm whether or not measurement preparation, i.e., attached condition of the pulse detection unit, is sufficient before starting measurement of the pulse rate.

It is also an object of the present invention to provide a portable pulse measuring device that displays information so that it is easy to read even without making the display device larger and that makes it possible to reduce the power consumed in displaying mode information.

It is still an object of the present invention to provide a portable pulse measuring device capable of correctly displaying the temporal progress of measurement results regardless of the length of the measurement time and without having to make the display device larger.

SUMMARY OF THE INVENTION

To achieve the above, this invention implements the display method in a portable pulse measuring device as described below.

According to a first aspect of the present invention, to allow the user to easily know his condition in detail by facilitating reading of displayed measured results the present invention accomplishes this by switching the graphic display mode between a first measurement period until the measured pulse rate reaches a prescribed value after graphic display of the pulse rate has started and a second measurement period after the pulse rate has reached the prescribed value in a portable pulse measuring device capable of measuring the pulse rate while being worn as well as graphically displaying temporal changes in the measured pulse rate on the display device.

When the portable pulse measuring device of this invention is used to monitor a runner's pulse rate during a marathon or while jogging, for example, the runner can easily know at what level his pulse rate is according to the display mode by merely glancing at the display device occasionally. Moreover, since the temporal changes in the pulse rate are displayed graphically, the runner can know his condition in detail. Further, even though the pulse rate will change quickly immediately after the start of a marathon, the display mode will still change automatically according to the level, and therefore an easy-to-read display can be performed according to the level of the pulse rate in a display area of limited size.

For example, a bar graph is displayed in a first measurement period that extends according to the absolute value of the measured pulse rate, and in a second measurement period, a bar graph that extends in the positive direction or the negative direction is displayed at each time interval according to the difference between the measured pulse rate and the prescribed reference pulse rate. By means of this configuration, even though the display area may be small, a detailed comparison with the pulse rate (physical condition) during training can be easily performed.

In accordance with a second aspect of the present invention, even after performing an external operation that stops the measurement of time that was performed together with the measurement of the pulse rate, it is desirable to graphically display temporal changes in the measured pulse in a mode different from the second measurement period while continuing to measure the pulse rate for a prescribed period. By means of this configuration, recovery of the pulse rate during marathon training, etc., can be known. In this case, as well, display of the recovery and display during time measurement use different display modes, and therefore it is easy to distinguish the pulse rate of which period is being displayed.

In accordance with a third aspect of the present invention, it is desirable to display the pulse rate immediately after or immediately before the external operation that stops the measurement of time is performed at the same time the current pulse rate is displayed for the prescribed time period. In this way, the pulse rate immediately after or immediately before the measurement of time is stopped can be easily compared to the subsequent pulse rate, thus making it easy to confirm recovery of the pulse rate.

In accordance with a fourth aspect of the present invention, the portable pulse measuring device may also be configured such that the contents of the graphic display can be switched between display of the temporal change in the pulse rate and display of the temporal change in the pitch sought based on the measured results of the acceleration sensor. In this case, it is desirable to make the graphic display mode for temporal changes in the pulse rate in the first and second measurement periods different from the graphic display mode for temporal changes in the pitch. For example, temporal changes in the pitch can be displayed in a segmented graph plotted at each time period corresponding to the absolute value of the pitch. By means of this configuration, the runner can easily distinguish what is currently being displayed by merely observing the display mode. Also, the runner can easily determine his physical condition in detail from the temporal changes in the pitch.

Next, for the purpose of making it possible to reliably confirm whether or not measurement preparation, i.e., attached condition of the pulse detection unit, is sufficient before starting measurement of the pulse rate, it is desirable that the pulse signal be graphically displayed in the display device from when the mode is switched to the pulse rate measurement mode based on an external operation until an external operation is performed that starts time measurement and that the pulse rate be graphically displayed in the display device after an external operation is performed that starts time measurement.

By means of this configuration, not only is it possible to reliably confirm that preparation for measurement of the pulse rate is complete by whether or not the pulse signal is being graphically displayed, it is possible to specifically judge from the waveform or level of the pulse signal whether or not the pulse detection unit is properly attached before starting measurement of the pulse rate. It is also possible to adjust the attached condition of the pulse detection unit while confirming the waveform or level. Further, this function can also be used to inspect for good and defective products in the production of pulse measuring devices. Moreover, since the waveform is displayed graphically, it is possible to confirm the stability of the time base.

In accordance with a fifth embodiment of the present invention, from when the mode is switched to the pulse rate measurement mode based on an external operation until processing that seeks the pulse rate becomes possible, it is desirable that information indicating same be displayed in the display device and that the pulse signal be displayed in the display device from the time processing that seeks the pulse rate becomes possible until an external operation that starts time measurement is performed. By means of this configuration, it is possible to reliably confirm that preparation for pulse rate measurement is complete by merely seeing that the pulse signal is being graphically displayed.

When the pulse rate is graphically displayed in this invention, it is desirable that the pulse signal be amplified until it is of a prescribed amplitude and that the amplitude level be displayed in the display device. By means of this configuration, the attached condition of the pulse detection unit can be accurately confirmed by considering the amplification level together with the original waveform of the pulse signal.

When graphically displaying the pulse wave in this invention, it is desirable that display be switched to newly measured pulse signals during normal power load but that during heavy power loads, such as when the backlight is on in the display device or when the alarm sounds, the display be fixed at the pulse signal that was being displayed until the heavy load condition is terminated. By means of this configuration, even if the pulse signal cannot be accurately detected during a heavy power load, the currently displayed waveform is graphically displayed in a fixed state instead of the newly measured pulse signal, and therefore an irregular waveform need not be displayed.

In accordance with a sixth embodiment of the present invention, for the purpose of displaying easy-to-read information without having to make the display device larger and to reduce the power consumption required to display mode information, it is desirable that information on the selected mode be displayed in the display device when the mode is selected by an external operation and that display of the mode information automatically turns off after a prescribed time has elapsed.

By means of this configuration, the information display eventually turns off, and therefore it is possible to display information that considers only ease of reading without having to provide a large dedicated display area for information display. Also, when the display is left off after information display has been performed, the fact that the information display itself is off means that a specific mode has been selected. Also, since display is performed only for the minimum time required for the user to confirm the mode, power is conserved. For this reason, the battery life can be extended in a multifunction portable pulse measuring device that can only hold small batteries from the standpoint of portability.

In accordance with a seventh embodiment of the present invention, it is desirable that the display device comprises a segment display area for displaying time information and a dot display area for graphically displaying various types of information, that information on the selected mode be displayed in the dot display area and that display of the mode information automatically turn off after a prescribed time has elapsed. By means of this configuration, information is displayed in the dot display area which is capable of displaying much information, and therefore the information is easy to read. In this case, as well, information display automatically turns off, and therefore power is conserved even if the power consumption of the dot display area is large.

Of the modes wherein display of information on the selected mode automatically turns off in this invention, after display of information on the selected mode is performed while the time mode is selected, it is desirable that display of information in the display area remain off. Since the frequency of returning to the time mode is high in a portable pulse measuring device, power conservation can be maximized when returning to this time mode if the mode information method of this invention is utilized.

Next, in this invention, for the purpose of accurately displaying temporal transitions in the pulse rate regardless of the length of the measurement time and without making the display device larger, it is desirable that the portable pulse measuring device comprise a plurality of data compression means capable of data compression with respect to time of ratio or rank of two or better of the measurement results of the pulse rate measured at each fixed time. A plurality of compressed data memory means stores the compressed data obtained by the data compression means. A data compression control means that controls the data compression means such that they recompress data stored in the compressed data memory means at a compression factor increased by ratio or rank of one when the number of data stored in these compressed data memory means reach a value set according to the compression ratio or rank and also such that they store subsequent data in the compressed data memory means as compressed data compressed at a compression factor increased by rank one, and that temporal changes in the pulse rate be graphically displayed on the display device based on the compressed data stored in the compressed data memory means.

In accordance with an eighth embodiment of the present invention, data compression is performed when the number of data increases, and therefore temporal transitions in the pulse rate can be appropriately displayed regardless of the length of the measurement time without having to expand the display device. Also, compressed data are not displayed as is, but rather the data stored in the compressed data memory means with the greatest number of data can be displayed, thus alleviating the problem of the number of data suddenly decreasing when data compression is used.

In accordance with a ninth aspect of the present invention, it is desirable that the data compression means comprise a first data compression means that doubles the compression factor after each time the number of data stored in the corresponding compressed data memory means reaches a set value after data compression of the measurement results is performed at a 1× compression factor and a second data compression means that doubles the compression factor after each time the number of data stored in the corresponding compressed data memory means reaches a set value after data compression of the measurement results is performed at a 3× compression factor, and that temporal changes in the pulse rate be graphically displayed on the display device based on the results of data processing by these two data compression means. That is, a first data compression means is provided that switches the compression factor from 1×, to 2×, 4×, 8×, etc., and a second data compression means is provided that switches the compression factor from 3× to 6×, 12×, 24×, etc., and therefore the compression factor switches almost continuously. For this reason, temporal changes in the pulse rate can be known in detail any time.

In accordance with a tenth aspect of the present invention, after completion of measurement, temporal changes in the pulse rate may be graphically displayed based on compressed data stored in the compressed data memory means of the plurality of compressed data memory means, and the greatest number of data are stored.

Further, when the number of data stored in the compressed data memory means reaches the set value and the compressed data stored there up to that point is recompressed at a compression factor one rank higher, it is judged at that point which compressed data memory means has the greatest number of data stored in it. The graphic display of temporal changes in the pulse rate is switched to display based on the compressed data stored in the compressed data memory means with the greatest number of data. In this case, display can be performed using compressed data even during measurement.

In accordance with an eleventh embodiment of the present invention, after completion of measurement, it is desirable that the compressed data stored in the compressed data memory means of the plurality of compressed data memory means with the greatest number of data stored in it be stored based on an external operation and that the temporal changes in the pulse rate be graphically redisplayed based on the compressed data.

Other objects and attainments together with a fuller understanding of the invention will become apparent and appreciated by referring to the following description and claims taken in conjunction with the accompanying drawings.

BRIEF DESCRIPTION OF THE DRAWINGS

In the drawings wherein like reference symbols refer to like parts

FIGS. 1A and 1B are diagrams showing the overall configuration of a portable pulse measuring device in accordance with the invention;

FIG. 2 is a plan view of the main unit of the portable pulse measuring device shown in FIGS. 1A and 1B;

FIG. 3 is a side view of the main unit of the portable pulse measuring device shown in FIGS. 1A and 1B taken from the 3 o'clock direction;

FIG. 4 is a cross-sectional view of a sensor unit of the portable pulse measuring device shown in FIGS. 1A and 1B;

FIG. 5 illustrates the sensor unit used in the portable pulse measuring device shown in FIGS. 1A and 1B as attached to a finger;

FIG. 6 is a schematic showing the electrical connection relationships in a connector of the portable pulse measuring device shown in FIGS. 1A and 1B;

FIG. 7 is a functional block diagram showing the control unit of the portable pulse measuring device shown in FIGS. 1A and 1B;

FIGS. 8, 8A and 8B is a functional block diagram showing the data processor and the display controller comprising the control unit shown in FIG. 7;

FIG. 9 depicts the display for each mode of the portable pulse measuring device shown in FIGS. 1A and 1B;

FIG. 10 shows the information display when the time mode of the modes shown in FIG. 9 is selected;

FIG. 11 shows the information display shown in FIG. 10 turned off;

FIG. 12 shows the content of the display when the time is set in the time mode shown in FIG. 9;

FIG. 13 is a flowchart showing the operation performed in the pulse data processor when changing to the pulse measuring mode shown in FIG. 9;

FIGS. 14, 14A and 14B are diagrams depicting the functions in the pulse measuring running mode in the portable pulse measuring device shown in FIGS. 1A and 1B;

FIG. 15 shows the display mode immediately after switching to the pulse measuring running mode shown in FIGS. 14A and 14B;

FIG. 16 shows the display mode immediately after completing preparation to start measurement after switching to the pulse measuring running mode shown in FIGS. 14A and 14B;

FIG. 17 shows the display mode in the first period until the number of pulses measured in the pulse measuring running mode shown in FIGS. 14A and 14B reaches the prescribed range;

FIG. 18 shows the display mode in the second period after the number of pulses measured in the pulse measuring running mode shown in FIGS. 14A and 14B reaches the prescribed range;

FIG. 19 shows the display mode of the pitch measured in the pulse measuring running mode shown in FIGS. 14A and 14B;

FIG. 20 shows the display mode until the prescribed time has elapsed after an operation that stops the measurement of time in the pulse measuring running mode shown in FIGS. 14A and 14B;

FIG. 21 shows the display mode when the prescribed time has elapsed and measurement of the pulse rate is completed after an operation that stops the measurement of time in the pulse measuring running mode shown in FIGS. 14A and 14B;

FIG. 22 is a functional block diagram of the data processor for display which comprises the control unit shown in FIGS. 7 and 8;

FIGS. 23, 23A and 23B are flowcharts showing the operation of the data processor for display shown in FIG. 22; and FIG. 24 shows the mode when the pulse rate is displayed based on compressed data obtained by the operation shown in FIGS. 23A and 23B.

DESCRIPTION OF THE PREFERRED EMBODIMENTS

Embodiments of the invention are described below based on the drawings.
Overall Configuration FIGS. 1A and B are explanatory diagrams showing the overall configuration of the portable pulse measuring device of this invention.

In FIGS. 1A and B, portable pulse measuring device 1 (wrist-worn pulse measuring device) of this embodiment roughly comprises main unit 10 having a wrist watch structure, cable 20 connected to this main unit 10, and sensor unit 30 (pulse signal detector) disposed on the end of cable 20. Wrist band 12 is disposed on main unit 10 from the 12 o'clock direction to the 6 o'clock direction and is wrapped around the wrist. Therefore, main unit 10 can be freely affixed to the wrist by means of wrist band 12.

Sensor unit 30 is affixed to the index finger between the base of the finger and the first knuckle while light is also blocked by means of sensor attachment band 40 (unit attachment means). Since sensor unit 30 is attached near the base of the finger like this, cable 20 can be short, and therefore cable 20 does not get in the way while running. Measurements of the temperature distribution from the palm to the tip of the finger show that while the temperature at the tip of the finger drops markedly when it is cold, the temperature at the base of the finger drops relatively little. Therefore, when sensor unit 30 is attached to the base of the finger, the pulse rate, etc., can be accurately measured even when running outside on a cold day.
Configuration Of Main Unit FIG. 2 is a plan view of the main unit of the portable pulse measuring device of this embodiment with the wrist band and cable removed and FIG. 3 is a side view the main unit of the portable pulse measuring device looking from the 3 o'clock direction.

In FIG. 2, main unit 10 is equipped with plastic watch case 11 (main unit case). Display device 13 (preferably comprises a liquid crystal display), which displays the pulse rate (pulse information) as well as the current time and date, is disposed on the front side of watch case 11. This liquid crystal display device 13 comprises first segment display area 131 disposed in the upper left of the display surface, second segment display area 132 disposed in the upper right, third segment display area 133 disposed in the lower right and dot display area 134 disposed in the lower left. Dot display area 134 is capable of graphically displaying various types of information. The power consumed to perform graphic display in dot display area 134 tends to be greater than the power consumed when performing segment display in first to third segment display areas 131–133.

Control unit 5 is disposed inside watch case 11 for the purpose of seeking the pulse rate based on detection results (pulse signal) from sensor unit 30 and displaying those temporal changes, etc., in liquid crystal display device 13. Control unit 5 has functions that control display in liquid crystal display device 13 and perform signal processing of the detection signal. Since control unit 5 also includes clock circuit 5, the regular time, lap time, split times, etc., can be displayed on liquid crystal display device 13.

Button switches 111–117 for performing operations that set the time, switch the mode, and start measurement of lap times and pulse information are disposed on the sides and front of watch case 11.

The power supply of portable pulse measuring device 1 is a button-shaped battery 59 built into watch case 11. Cable 20 supplies power from battery 59 to sensor unit 30 and also inputs the detection results from sensor unit 30 to control unit 5 in watch case 11.

With these added functions, it is necessary to increase the size of main unit 10 in portable pulse measuring device 1, but main unit 10 is restricted because it is attached to the wrist. Therefore, main unit 10 cannot be increased in size in the 6 o'clock or 12 o'clock directions on the watch. For this reason, wide watch case 11 which is wider in the 3 o'clock and 9 o'clock direction than in the 6 o'clock and 12 o'clock direction is used for main unit 10. However, since wrist band 12 is attached at a location toward the 3 o'clock side, there is a large protruding member 101 in the 9 o'clock direction on the watch as seen from wrist band 12, but there is no large protruding member in the 3 o'clock direction. Therefore, even though wide watch case 11 is used, the wrist can bend freely, and even if the user should fall down, watch case 11 will not strike the back of the hand.

A buzzer comprising, for example, flat piezoelectric element 58 is disposed in watch case 11 in the 9 o'clock direction with respect to battery 59. Since battery 59 is heavy compared to piezoelectric element 58, the center of gravity of main unit 10 is at a location shifted toward 3 o'clock. Since wrist band 12 is attached on the side toward which the center of gravity is shifted, main unit 10 can be worn on the wrist in a stable condition. Also, since battery 59 and piezoelectric element 58 are disposed in the same plane, main unit 10 can be made thin, and as shown in FIG. 3, the user can easily replace battery 59 by providing battery cover 118 on back surface 119.

Structure For Attaching Main Unit To Wrist

In FIG. 3, linkage member 105 is disposed in the 12 o'clock direction on watch case 11, and wrist band pin 121 affixed to the end of wrist band 12 is held in linkage member 105. Holder 106 is disposed in the 6 o'clock direction on watch case 11, and fastener 122 which holds the folded-back part of wrist band 12 wrapped around the wrist is affixed to holder 106.

The member extending from back surface 119 toward holder 106 in the 6 o'clock direction of main unit 10 is rotation inhibitor 108 which forms an angle of approximately 115° with respect to back surface 119. That is, when main unit 10 is worn by means of wrist band 12 such that it is positioned on the top surface L1 (back of hand side) of the left wrist L (arm), back surface 119 of watch case 11 fits tight against the top surface L1 of the wrist L while rotation inhibitor 108 is in contact with the side surface L2 toward the radius R. In this state, back surface 119 of main unit 10 feels like it straddles the radius R and ulna U, while the surface extending from curved area 109 of rotation inhibitor 108 and back surface 119 to rotation inhibitor 108 feels like it is contact with the radius R. Since rotation inhibitor 108 and back surface 119 form an anatomically ideal angle of approximately 115°, main unit 10 will not shift unnecessarily even if it is turned in the direction of arrow A or in the direction of arrow B. Further, rotation of main unit 10 is only restricted by back surface 119 and rotation inhibitor 108 at two locations around the arm. For this reason, even if the arm is narrow, back side 119 and rotation inhibitor 108 are securely in contact with the arm, and therefore rotation is reliably inhibited, while if the arm is large, it will not feel confined.

Configuration Of Sensor Unit

FIG. 4 is a cross-sectional view of sensor unit 30 of the present embodiment.

In FIG. 4, component housing area 300 is formed in sensor unit 30 by being covered by back cover 302 on the back side of sensor frame 36 as the case unit. Circuit board 35 is disposed in component housing area 300. LED 31, phototransistor 32 and other electronic components are mounted on circuit board 35. The end of cable 20 is fixed in sensor unit 30 by bushing 393. Each of the wires of cable 20 is soldered to each of the patterns on circuit board 35. Here, sensor unit 30 is attached to the finger such that cable 20 is lead from the side toward the base of the finger toward the side of main unit 10. Therefore, LED 31 and phototransistor 32 are oriented along the length of the finger. Moreover, LED 31 is located on the side toward the end of the finger, and phototransistor 32 is located on the side toward the base of the finger. By disposing them this way, it is difficult for external light to reach phototransistor 32.

In sensor unit 30, a light transmission window is formed on the top (actual pulse signal detection member) of sensor frame 36 from transparent panel 34 made from glass. The light emitting surface and photoreceptor surface of LED 31 and phototransistor 32, respectively, are pointed toward light transmission panel 34. Therefore, when the surface of the finger is pressed against outside surface 341 (surface in contact with finger surface/sensor surface) of transparent plate 34, it is possible for LED 31 to emit light toward the finger surface and for phototransistor 32 to receive the light emitted by LED 31 that is reflected back from the finger. Here, for the purpose of improving the contact between outside surface 341 of transparent plate 34 and the finger surface, a structure is employed wherein outside surface 341 of transparent plate 34 protrudes beyond surrounding member 361.

In this embodiment, an InGaN (indium-gallium-nitrogen) type blue LED is used as LED 31. The light emitting spectrum has a peak at 450 nm, and the light emitting wavelength range is from 350 to 600 nm. A GaAsP (gallium-arsenic-phosphorous) type phototransistor is used as phototransistor 32 to correspond with LED 31 having these light emitting characteristics. The photoreceptor wavelength range of the element itself comprises a principal sensitivity range of 300 to 600 nm and also a sensitivity range below 300 nm.

Sensor unit 30 configured in this manner is attached to the base of the finger by band for securing sensor 40 (not shown in FIG. 5) as shown in FIG. 5, light is irradiated toward the finger from LED 31 in this state, and this light arrives at the blood vessels where some is absorbed by the hemoglobin in the blood and some is reflected back. The light reflected back from the finger (blood vessels) is received by phototransistor 32, and changes in the amount of light received correspond to changes in the amount of blood (pulse of blood). That is, since the reflected light weakens when there is much blood and the reflected light strengthens when there is little blood, the pulse rate, etc., can be measured by detecting changes in the intensity of the reflected light.

LED 31 with a light-emitting wavelength range of 350 to 600 nm and phototransistor 32 with a photoreceptor wavelength range of 300 to 600 nm are used in this embodiment, the pulse signal is detected based on detection results obtained in the overlapping wavelength range from about 350 nm to about 600 nm, i.e., wavelength range below about 700 nm. By using this kind of sensor unit 30, even when external light strikes the exposed areas of the finger, light included in the external light with a wavelength of less than 700 nm does not arrive at phototransistor 32 (photoreceptor unit) with the finger acting as a light guide. The reason is because light included in the external light with a wavelength of less than 700 nm does not readily pass through the finger, and even when the area of the finger not covered by band for securing sensor 40 is exposed to external light, it does not travel through the finger and arrive at phototransistor 32 as indicated by the dashed line X. When an LED with a light-emitting peak near 880 nm and a silicon type phototransistor are used, however, the wavelength range of received light is from 350 to 1200 nm. Therefore, since the pulse is detected based on detection results obtained using light with a wavelength of 1 μm, which readily arrives at the photoreceptor unit via the finger acting as a light guide as indicated by arrow Y in FIG. 5, errors will readily occur due to fluctuations in the external light.

Also, since the pulse signal is detected using light with a wavelength less than about 700 nm, the S/N ratio of the pulse signal based on changes in the amount of blood is high. The reason for this is because the light absorption coefficient of hemoglobin for light with wavelengths from 300 to 700 nm is from several ten to several hundred times greater than that for light with wavelengths greater than 880, which is the detection light used in the prior art, and therefore since it changes with high sensitivity to changes in the amount of blood, the detection rate (S/N ratio) of the pulse based on changes in the amount of blood is high.

In FIG. 5, terminal 38 is disposed around transparent plate 34 for grounding to the body.

In this example, detection of the pulse signal from the body was performed on the finger, but the location is not restricted and can be performed around the wrist as well. Also, instead of an optical method, a pressure sensor, or the like, can be used as the detection method.

Structure Of Connection Between Main Unit And Sensor Unit

As shown in FIGS. 1A and 3, connector member 70 is disposed on the front side of the member extending from main unit 10 in the 6 o'clock direction as rotation inhibitor 108, and connector piece 80 disposed on the end of cable 20 is configured such that it can be attached to and detached from connector member 70. Therefore, by removing connector piece 80 from connector member 70, portable pulse measuring device 1 can be used as a regular watch or stop watch. However, a prescribed connector cover is attached for the purpose of protecting connector member 70 when used with cable 20 and sensor unit 30 detached from connector member 70 of main unit 10. A unit configured in the same way as connector piece 80 can be used as the connector cover. However, the connector cover does not require electrodes, etc.

In the connector structure configured in this manner, connector member 70 is in front as seen by the user, thus simplifying operation. Also, since connector member 70 does not protrude from main unit 10 in the 3 o'clock direction, the user is free to move his wrist while running and connector member 70 will not strike against the back of his hand should he fall while running.

The electrical connections in the connector configured from connector member 70 and connector piece 80 are shown in FIG. 6.

In FIG. 6, terminals 751 to 756 (first terminal group) are disposed on connector member 70 disposed on the main unit 10 side, and electrodes 831 to 836 (second terminal group) are configured on connector piece 80 to correspond to these terminals 751 to 756. Of these, terminal 752 is a plus terminal for supplying second drive voltage VDD to LED 31 via electrode 832, terminal 753 is made the minus potential of LED 31 via electrode 833, terminal 754 supplies constant voltage VREG for drive to the collector terminal of phototransistor 32 via electrode 834, and terminal 751 inputs the signal from the emitter terminal of phototransistor 32 via electrode 831.

Terminal 755 inputs the signal for detecting whether or not connector piece 80 is connected to connector 70 via electrode 835, and when connector piece 80 is connected to connector member 70, a signal indicating same is input to control unit 5 of main unit 10 via connector member 70.

Electrode 836 provides a ground to the body via terminal 38 for body ground in sensor unit 30, and when terminal 756 and electrode 836 are electrically connected, electrodes 831 to 836 become shielded by making VDD a ground line.

In connector piece 80, first capacitor C1 and first switch SW1 are inserted between the terminals (between electrodes 832 and 833) of LED 31. When connector piece 80 is disconnected from connector member 70, this switch SW1 goes to a closed condition, whereby first capacitor C1 is connected in parallel to LED 31, and when connector piece 80 is connected to connector member 70, switch SW1 goes to an open condition. Similarly, second capacitor C2 and second switch SW2 are inserted between the terminals (electrodes 831, 834) of phototransistor 32. When connector piece 80 is disconnected from connector member 70, this switch SW2 also goes to a closed condition, whereby second capacitor C2 is connected in parallel to phototransistor 32, and when connector piece 80 is connected to connector member 70, switch SW2 goes to an open condition. Therefore, even if electrodes 831, 832, 833, 834, which have a high potential due to static electricity, are touched when connector piece 80 is disconnected from connector member 70, that electric charge is stored in first and second capacitors C1 and C2 and LED 31 and phototransistor 32 are not damaged. When connector piece 80 is connected to connector member 70, pulse signal detection is automatically enabled.

Overall Configuration Of Control Unit

FIG. 7 is functional block diagram of control unit 5 disposed inside main unit 10 of the portable pulse measuring device of this embodiment, and FIG. 8 is another functional block diagram of the data processor 55 and display controller 53 disposed in the control unit. In FIGS. 7, 8, 8A and 8B, the operations performed by control unit 5, data processor 55, display controller 53 and display switching controller 530 are performed based on programming stored in the CPU, and therefore those functions are depicted in a block diagram.

In FIG. 7, two integrated circuits or IC's 50, 56 are disposed in control unit 5.

IC 56 comprises timer 561 which performs timer operations based on the signal from an oscillation circuit equipped with a crystal oscillator and a variable capacitor, voltage booster circuit 541 for liquid crystal display which obtains the voltage for performing the prescribed display in liquid crystal display device 13, and drive circuit 562 for liquid crystal display that drives liquid crystal display device 13.

IC 56 also includes mode switching unit 564 which performs control for switching portable pulse measuring device 1 to the clock mode, the regular stopwatch mode and the pulse measuring mode wherein the pulse rate is measured, and display controller 53 which controls processing of information to be displayed in liquid crystal display device 13 according to the active mode at that time.

IC 50 includes pulse data processor 55 which determines the pulse rate, etc., based on input results from sensor unit 30 and facilitates display of information on liquid crystal display device 13 by outputting the pulse rate or other measurement results to IC 56 (display controller 53).

The clock signal for operation by each of the components is output from IC 56.

In control unit 5, capacitance elements 528, 558 are connected in parallel with respect to battery 59, and of these, capacitance element 528 serves as a backup capacitor for memory 563, etc., built into IC 56. Capacitance element 558, however, is a backup capacitor for memory 501 built into IC 50. Voltage detector 543 for detecting the voltage between the terminals of battery 59 and inputting the detection result to IC 56 is disposed in main unit 10. When the voltage between the terminals of battery 59 drops below a threshold voltage, then information to that effect is displayed in liquid crystal display device 13. Piezoelectric element 58 for generating a notification sound and voltage booster circuit 580 for notification sound generation, which is equipped with a coil for boosting the voltage applied to piezoelectric element 58, are also disposed inside main unit 10.

Configuration Of Pulse Data Processor

As shown in FIGS. 8A and 8B, in pulse data processor 55, after the signal from sensor unit 30 is input to pulse signal amplifier 550, which is comprised by, for example, an operational amplifier, this signal is converted to a digital signal by pulse signal converter 551, which is implemented by an A/D converter, and is output to pulse signal memory 552. Pulse signal memory 552 is, for example, a random access memory (RAM) that stores to a digital signal representation of the pulse data. Pulse signal operation unit 553 reads the signal stored in pulse signal memory 552, performs frequency analysis (high speed Fourier transformation processing) on it and inputs the result to pulse component extraction unit 554. Pulse component extraction unit 554 extracts the pulse component from the output signal of pulse signal operation unit 553 and outputs it to pulse counter 555, where the pulse rate is calculated from the frequency component of the input pulse wave, and this result is output to the working memory of display controller 53.

In this embodiment, it takes 4 seconds to obtain one pulse rate datum, and pulse data processor 55 outputs the measurement results of the pulse rate to working memory 61 as data for display control every 4 seconds.

Configuration Of Pitch Data Processor

Acceleration sensor 91 and pitch data processor 92 which determines the pitch during running, based on the detection result of this sensor, are also disposed in portable pulse measuring device 1. Pitch data processor 92 outputs the pitch it obtains to working memory 533 of display controller 53.

Configuration Of Display Controller

Display switching controller 530 is disposed in display controller 53, and display switching controller 530 has a function that automatically changes the display mode of liquid crystal display device 13 based on the contents of the pulse rate data or instructions input via button switches 111 to 117.

Waveform data converter 531 and sweep display processor 532 are disposed in display controller 53. Waveform data converter 531 and sweep display processor 532 perform processing to graphically display (sweep display) the basic waveform of the pulse signal based on the pulse signal converted to a digital signal by pulse signal converter 551.

Amplitude monitor 534 which monitors the level of the pulse signal is disposed in display controller 53, and waveform signal amplifier 536 which switches the amplification factor in a plurality of steps when the pulse data are converted to waveform data based on the results monitored by amplitude monitor 534 is disposed in waveform data converter 531. Therefore, if the amplitude of the waveform signal is small in the results monitored by amplitude monitor 534, the waveform signal is amplified by a larger amplification factor, thus making it possible to graphically display the base waveform of the pulse signal in liquid crystal display device 13 in an appropriate size. Also, as described below, in order to allow the user to confirm proper attachment of sensor unit 30 to the finger by observing the base waveform of the pulse signal, display controller 53 also displays the amplification level at this time in liquid crystal display device 13.

Display controller 53 also includes load state monitor 535 which monitors the load state. When the load is high such as when the EL backlight is on in liquid crystal display device 13 or the alarm sounds, sensor unit 30 cannot correctly detect the pulse signal. Therefore, the waveform data output from waveform data converter 531 is temporarily stored in waveform data memory 538, and from the time it is determined in the monitor results of load state monitor 535 a high load state exists until the high load state is terminated, display switching controller 530 graphically displays the currently displayed waveform in a fixed state based on the waveform data stored in waveform data memory 538 instead of graphically displaying a newly measured pulse signal.

Pulse rate range memory 539 which stores a specified pulse range set in advance by external input as a pulse range and stores an interval roughly equivalent to this intermediate value as the reference pulse rate is disposed in display controller 53. The pulse rate range and reference pulse rate are data input by the user based on the results of previous training, etc.

Mode Switching Operation By Button Switches

The overall operation of portable pulse measuring device 1 is explained below. The modes explained here are specified by external operations (operation of buttons switches 111 to 117), and based on specification results, mode switching unit 564 shown in FIGS. 7 and 8 switches portable pulse measuring device 1 to the time mode, stopwatch mode or combined timer and pulse measuring mode. During this period, display controller 53 controls all operations related to display performed in liquid crystal display device 13, and display switching controller 53 controls switching of display performed in liquid crystal display device 13.

FIG. 9 shows each of the modes performed by portable pulse measuring device 1 and the contents of the display in liquid crystal display device 13 at that time.

In FIG. 9, step ST11 is the time mode, and the date, for example, Dec. 6, 1994 and Monday are displayed in first segment display area 131 and the current time 10:08:59 is displayed in second segment display area 132. "TIME" is displayed in dot display area 134 to indicate that the current mode is the time mode. However, as described below, the display of "TIME" in dot display area 134 lasts for only for a few seconds immediately after the time mode is selected. In this mode, nothing is displayed in third segment display area 133.

When button switch 111 at the 2 o'clock position is depressed in the time mode in portable pulse measuring device 1 of this embodiment, an alarm sound can be generated after 1 hour has elapsed, for example. The time at which this alarm sounds can be set as desired by an external operation. Also, when button switch, 113 at the 11 o'clock position is depressed, the EL backlight of liquid crystal display device 13 turns on for 3 seconds, and then turns off automatically.

When button switch 112 at the 4 o'clock position is depressed in this mode, the mode changes to the running mode (step ST12). In this mode, portable pulse measuring device 1 functions as a stopwatch. Before starting the measurement of time in the running mode (standby mode), the current time is displayed in first segment display area 131, and "0:00':00"00" is displayed in second segment display area 132. After "RUN" is displayed in dot display area 134 for only 2 seconds to indicate the running mode, the display changes to graphic display.

When button switch 112 at the 4 o'clock position is depressed in this mode, the mode changes to the lap time recall mode (step ST13). This mode is used to read out lap times and split times previously measured using portable pulse measuring device 1. In the lap time recall mode, the date is displayed in first segment display area 131 and the current time is displayed in second segment display area 132. "LAP/RECALL" is displayed in dot display area 134 for only 2 seconds to indicate the recall mode, and then the transition in the pulse rate with each new lap is displayed.

When button switch 112 at the 4 o'clock position is depressed in this mode, the mode changes to the pulse measuring result recall mode (step ST14). This mode is used to read out temporal changes in the pulse rate previously measured using portable pulse measuring device 1. Portable pulse measuring device 1 also has a function that measures temporal changes in the pitch during a marathon using the acceleration sensor in main unit 10 and a function that stores the results, and therefore temporal changes in previously measured pitches can be read out in this mode. In the recall mode for measured pulse results, the date is displayed in first segment display area 131 and the current time is displayed in second segment display area 132. "RESULT/RECALL" is displayed in dot display area 134 for only 2 seconds and then a graph showing the temporal changes in the average pulse rate is displayed.

When button switch 112 at the 4 o'clock position is depressed in this mode, then the mode returns to the time mode (step ST11) as indicated by arrow P1. Also, if there is no input for 10 minutes in steps ST12 to ST14, then the mode returns to the time mode (step ST11) as indicated by arrow P2. When the mode returns to this time mode, the date is displayed in first segment display area 131 and the current time is displayed in second segment display area 132.

When the time mode is set as described above, "TIME" is displayed in dot display area 134 to indicate the time mode as shown in the enlargement of liquid crystal display device 13 in FIG. 10. This information display, as shown in FIG. 11, turns off automatically after 2 seconds and the display goes to the regular time mode state (step ST15). In this regular time mode state, nothing is displayed in dot display area 134.

When button switch 112 at the 4 o'clock position is pulled out only one step in this time mode, the mode changes to the date and time setting mode.

That is, as shown in FIG. 12, when button switch 112 at the 4 o'clock position is pulled out only one step in the regular time mode state (step ST15), the second setting mode is set first (step ST21). When button switch 117 positioned at the top on the front of main unit 10 is depressed in this mode, the seconds are incremented by 1. When the button switch at the 7 o'clock position is depressed in this mode, the minute setting mode is set (step ST22). Each time the button switch at the 7 o'clock position is depressed following this, the mode changes to the hour setting mode (step ST23), the year setting mode (step ST24), the month setting mode (step ST25), the day setting mode (step ST26), and the 12 hour/24 hour selection mode (step ST27), and if depressed again, the mode returns to the second setting mode (step ST21).

During this time, regardless of what mode you are in, the mode changes to the time mode when button switch 112 at the 4 o'clock position is depressed. At this time, as well, as described in FIGS. 10 and 11, when returning to the time mode (step ST11), "TIME" is displayed in dot display area 134 for only 2 seconds, after which this information display turns off automatically and the regular time mode state is established (step ST15).

In this way, when returning to the time mode (step ST11), "TIME" is displayed for only 2 seconds in dot display area 134 to indicate the time mode has been selected, and after 2 seconds, this information display turns off automatically and the regular time mode state is established (step ST15). That is, by performing dot display for the minimum amount of time required to tell the user the mode and using a mode display wherein the fact that it is off lets the user know that the regular time mode state has been established, power is conserved in the display of information. For this reason, even though much power is consumed due to the multiple functions added to portable pulse measuring device 1 so that it can be used as a pulse measuring and pitch counter, the life of battery 59 is long in view of the fact that small, compact button-shaped battery 59 is used as the only power source in order to maintain portability. Dot display area 134, in particular, though convenient for displaying mode information in detail because of its ability to display much information, consumes much power, and therefore display time is kept to a minimum number of seconds, thereby solving the problem of the greater power consumption of dot display area 134 than in first to third segment display areas 131 to 133. For this reason, power is conserved as well as making mode information easy to read by means of this invention. Further, when the time mode is selected, which is the most commonly performed operation in portable pulse measuring device 1, the effect of power conservation is large because the power-saving mode information method described above is used.

Changing To Pulse Measuring Mode

When portable pulse measuring device 1 is being used as a regular wrist watch, no power is supplied to pulse data processor 55 or sensor unit 30, and power is supplied when portable pulse measuring device 1 is changed to the pulse measuring mode. Initialization processing, such as setting the operation period in the A/D converter which makes up pulse signal converter 551 in data processor 55, is performed when this power is first supplied.

Operation of pulse data processor 55 configured like this is controlled based on instructions from mode switching unit 564 and display controller 53. This operation is described by referring to the flowchart in FIG. 13.

In FIG. 13, when mode switching unit 564 changes portable pulse measuring device 1 to the pulse measurement mode in step ST1, power is supplied to pulse data processor 55 and sensor unit 30 in step ST2. Switching to this mode is performed automatically based on the external operation of connecting connector piece 80 to connector member 70.

Following this, in step ST3, initialization processing such as setting the operation period in the A/D converter which comprises pulse signal converter 551 is performed. In this embodiment, digitalization of the pulse signal by pulse signal converter 551 is performed in 4-second periods, and therefore the device is in standby in step ST4 until this conversion is complete. During this time, display is performed in liquid crystal display device 13 as described below.

Next, after digitalization of the pulse signal of one period, display controller 53 judges whether or not the measurement of time was started by an external operation in step ST5. When button switch 117 is depressed as this external operation after changing to the measurement mode for pulse information, display controller 53 judges that there was an instruction to start time measurement. The means for starting time measurement using button switch 117 is configured like this in this embodiment.

If display controller 53 determines that the external operation to start the measurement of time was not performed in step ST5, then the digitized pulse signal is converted to a waveform by waveform data converter 531 and sweep display controller 532 in step ST6, and the base waveform of the pulse signal is graphically displayed in liquid crystal display device 13 (step ST7) as described below.

If display controller 53 determines that the external operation to start the measurement of time was performed in step ST5, however, then the signal stored in pulse signal memory 552 is read out to pulse signal operation unit 553 where it undergoes frequency analysis in step ST8, and the result is input to pulse component extraction unit 554 in step ST9 where it is converted to pulse data. In step ST7, the pulse rate is displayed in liquid crystal display device 13.

After completion of processing in step ST7, then the above processing is repeated from step ST4. Therefore, the latest pulse rate can be displayed in liquid crystal display device 13.

Since portable pulse measuring device 1 can also be used as a stopwatch as well as a pulse measuring in this mode, it can be referred to as a pulse measuring running mode rather than simply a running mode.

Pulse Measuring Running Mode

Regardless of what mode portable pulse measuring device 1 is in, when connector piece 80 is connected to connector member 70, a signal indicating same is automatically input to controller 5 (mode switching unit 564), and as a result the mode changes to the running mode (step ST12) as indicated by arrow P3 in FIG. 9. This running mode not only operates as a stopwatch, it is also capable of measuring the pulse rate (pulse measuring running mode).

The operation of the pulse measuring running mode and the display modes performed in this mode are explained using FIGS. 14, 14A and 14B.

FIGS. 14A and 14B is a functional block diagram of the pulse measuring running mode in the portable pulse measuring device shown in FIGS. 1A and 1B. In this mode, as well, display controller 53 controls all operations related to display performed in liquid crystal display device 13, and display switching controller 53 controls the switching of display performed in liquid crystal display device 13.

Display Modes During Preparation

In FIGS. 14A and 14B, immediately after changing to the pulse measuring running mode (step ST31) by the external operation of connecting connector piece 80 to connector member 70, the current time is displayed in first segment display area 131, "0:00':00":00" is displayed in second segment display area 132, and "RUN" is displayed in dot display area 134 of liquid crystal display device 13, as shown in detail in FIG. 15. Also, the heart mark flashes in third segment display area 133 to indicate the pulse measuring running mode has been set.

By changing the mode, power is supplied to pulse data processor 55 shown in FIGS. 7 and 8 as described above, and initialization processing such as setting the operation period in the A/D converter which makes up pulse signal converter 551 is performed.

Two seconds after this initialization processing is begun, a pulse signal is obtained to measure the first pulse rate. At this time, the display of "STOP/5" (step ST32) and the display of "MOTION/4" (step ST33) are alternated in dot display area 134 at a frequency of 2 Hz for five seconds to indicate no motion. The number displayed at this time changes to indicate a 5-second count down.

While this initialization processing is performed in data processor 55, information indicating same is displayed in liquid crystal display device 13. In the display of information, various messages and characters can be displayed.

After the initial pulse rate value is measured, then the device goes to a standby state until button switch 117 is depressed to start the measurement of time (step ST34).

In this standby state, the base waveform of the pulse signal is graphically displayed in dot display area 134. The base waveform displayed here is the latest data. The initial pulse rate "75" is displayed in third segment display area 132.

Since the display shown in FIG. 15 is performed during the period measurement of the pulse signal cannot begin after changing to the measurement mode for pulse information, and the display shown in FIG. 16 is performed after processing that seeks pulse information becomes possible, it is possible to confirm that preparation for measurement of pulse information has been completed after the display switches to display of the base waveform. Therefore, mistakes such as missing the timely measurement of the pulse rate during a marathon will not be made. This kind of function can also be used for inspection in the production of portable pulse measuring device 1. Further, since the base waveform is graphically displayed, it is possible to confirm from the state of the display whether or not the time base is changing due to wear of the battery, etc. Moreover, it is possible to confirm from the waveform in advance whether or not the ambient temperature or humidity provide an environment that allows measurement. When the base waveform of the pulse signal is graphically displayed, the waveform of the pulse signal is amplified to a prescribed amplitude, and therefore indicator MM is displayed in first segment display area 131 to indicate the amplification level is "2." For this reason, the base waveform of the pulse signal is graphically displayed in liquid crystal display device 13 in an appropriate size. If the user confirms the waveform of the pulse signal and the amplification level at this time before the user starts the measurement of time (marathon), the user can judge whether or not sensor unit 30 (LED 31 and phototransistor 32) is correctly attached to the finger. Also, by adjusting LED 31 or phototransistor 32 while checking the waveform and amplification level, the user can adjust LED 31 and phototransistor 32 at the optimum position. That is, after attaching sensor unit 30 to the finger, the user confirms whether or not the waveform of the pulse signal is being graphically displayed in liquid crystal display device 13, and if the waveform is being graphically displayed, then the user adjusts the attached condition of sensor unit 30 until the amplification level (indicator MM) shown in first segment display area 131 is as small as possible.

If the EL backlight turns on in liquid crystal display device 13 at this time, the drive voltage drops, and therefore the pulse signal cannot be correctly detected. Therefore, instead of graphically displaying a base waveform based on a newly measured pulse signal in this embodiment, the currently displayed waveform is graphically displayed in a fixed state. This prevents spurious waveforms from being displayed in liquid crystal display device 13.

When button switch 117 positioned at the top on the front of main unit 10 is depressed in this state at the same time the marathon starts, the measurement of time is started. Also, the measurement of the pulse rate is continued (step ST35).

Display Mode In First Period

After the measurement of time is started in this way, the pulse rate data output from pulse data processor 55 with the passage of time is stored in working memory 61 in display controller 53.

At this time, as shown in FIG. 17, first the time is displayed in second segment display area 132, and the pulse data stored in working memory 61 is graphically displayed as temporal changes in the pulse rate in dot display area 134. The graphic display performed at this time comprises a display of the absolute value in a vertical bar graph extending up using roughly the middle position of the vertical axis as pulse rate 65. During this time, the graduation on the vertical axis of the graph shown in dot display area 134 and the pulse rate at that time are displayed in third segment display area 133.

While the absolute value of the pulse rate is displayed in dot display area 134 in this way, display switching controller 530 compares the measured pulse rate with the pulse rate range stored in pulse rate range memory 539.

Here, when it is judged that the measured pulse rate is not within the pulse rate range (first measurement period), then the new pulse rate continues to be displayed in a vertical bar graph that extends up as shown in FIG. 17.

Display Mode In Second Period

If, however, display switching control unit 530 judges that the measured pulse rate is within the pulse rate range (pulse rate is between 120 and 168) stored in pulse rate range memory 539, that is, when the pulse rate reaches the lower limit of 120, then following this (second period), as shown in FIG. 18, a bar graph that extends in the positive direction or the negative direction is displayed in dot display area 134 of liquid crystal display device 13 (step ST36) at each time interval according to the difference between the measured pulse rate and the reference pulse rate (pulse rate of 150) stored in pulse rate range memory 539. The display shown in FIG. 18 is an example wherein approximately the middle position of the vertical axis is pulse rate 150 and a bar graph that extends above and below (positive and negative directions) this by an amount equivalent to the difference from this value is displayed. Here, the pulse rate range and reference pulse rate are data the user has input based on the results of previous training, etc., and as shown in the right side of dot display area 134 in FIG. 18, the pulse rate range "120 to 168" is indicated by bracket mark indicator MA.

As described above, display switching controller 530 automatically switches the mode of graphic display in dot display area 134 between the first measurement period and the second measurement period. Therefore, when portable pulse measuring device 1 is used in a marathon to monitor the pulse rate, the runner can easily know at about what level his pulse is by seeing the display mode when he occasionally looks at dot display area 134 even if dot display area 134 is small. Moreover, temporal changes in the pulse rate are displayed there, and so he can know his condition in detail. Further, though the pulse rate will change quickly immediately after a marathon is started, since the display mode when the measured pulse rate is within the range is different from that when the measured pulse rate is not within the range, an easy-to-read display corresponding to the pulse rate level can be performed in dot display area 134 whose area is limited.

Until the pulse rate reaches the prescribed range, a bar graph that extends at each time interval is displayed according to the absolute value of the pulse rate, and after the pulse rate reaches the prescribed range, a bar graph is displayed that extends in the positive or negative direction at each time interval according to the difference from the prescribed reference pulse rate. For this reason, even if dot display area 134 is small, detailed comparisons with the physical condition during training can be easily performed.

Display Mode For Pitch

As shown in FIGS. 8A, 8B, 14A and 14B, the pitch data sought by pitch data processor 92 based on the detection results of acceleration sensor 91 are stored in working memory 533 of display controller 53 in portable pulse measuring device 1. Therefore, even if the pulse rate is being measured, when button switch 14 at the 8 o'clock position is depressed, display switching controller 530 graphically displays temporal changes in the pitch in a segmented graph plotted at each time period corresponding to the absolute value of the pitch (step ST37) in dot display area 134 of liquid crystal display device 13. Here, since pitch 170 is set as the target pitch, the segmented graph is plotted against a vertical axis whose middle position is pitch 170. At this time, the graduation on the vertical axis of the graph (indicator showing that the middle position on the vertical axis is pitch 170) displayed in dot display area 134 and the pitch at that time are displayed in third segment display area 133.

Since the display mode of temporal changes in the pitch in dot display area 134 differ from either of the display modes of the pulse rate in the first and second measurement periods in dot display area 134, the runner can easily judge which information is currently being displayed by merely looking at the display mode, and he can easily judge his specific physical condition from the temporal changes in the pitch.

When button switch 114 at the 8 o'clock position is depressed again in this state, dot display area 134 returns to the display of temporal changes in the pulse rate (step ST36).

When button switch 116 positioned at the bottom on the front of main unit 10 is depressed, the lap time at that time is displayed in first segment display area 131 (step ST38). Also, processing automatically returns to step ST36 10 seconds later.

Display Mode Of Recovery

Later, when button switch 117 positioned at the top on the front of main unit 10 is depressed at the same time the runner arrives at the goal, the measurement of pitch and time is stopped and "COOLING/DOWN" is displayed in dot display area 134 (step ST39).

After 2 minutes elapses in this state, the temporal changes in the pulse rate after reaching the goal are graphically displayed in dot display area 134 as the pulse recovery characteristic (step ST40). That is, mode switching unit 564 maintains the mode that continues to measure the pulse rate for a prescribed period, and display controller 53 graphically displays temporal changes in the pulse rate measured during this period as pulse rate recovery in dot display area 134.

In the graphic display of this pulse recovery, first the display changes to display of a vertical bar graph that extends up as shown in FIG. 20. In FIG. 20, the graph displayed in dot display area 134 shows the transition in the pulse rate every 4 seconds and that the measurement of time was stopped at the indicator MB point. In this way, graphic display after the indicator MB point is an absolute value display, which differs from the dot display mode in the second measurement period. That is, recovery of the pulse rate after the measurement of time is stopped when the runner crosses the marathon goal is displayed in a different graphic display.

When 16 seconds elapses in this state, i.e., upon completion of the measurement of four pulse rates, temporal changes in the pulse rate for 2 minutes after the measurement of time is stopped are graphically displayed in a bar graph in dot display area 134. That is, 30 temporal transitions in the pulse rate every 4 seconds are displayed in dot display area 134 from immediately before or immediately after the measurement of time is stopped. After the pulse rate is displayed for 2 minutes after the measurement of time is stopped, measurement of the pulse rate is stopped.

While graphically displaying pulse recovery in this way, the pulse rate immediately after or before stopping the measurement of time is indicated by indicator MC, and indicator MB of the graph and indicator MC of the pulse rate are flashed on and off to emphasize that this is pulse data from immediately before or after stopping the measurement of time.

Further, by displaying the current pulse rate in third segment display area 133 and comparing it with the pulse rate immediately before or after stopping the measurement of time, recovery of the pulse rate can be confirmed. It is generally said that when the pulmonary function is good, the time required for the pulse to recover is short.

In this way, since the measurement of the pulse rate is continued for a prescribed period after an external operation has been performed to stop the measurement of time and temporal changes in the pulse rate measured during this period are graphically displayed, it is possible to grasp the recovery of the pulse rate during training for a marathon, etc. Moreover, since the graphic display of the recovery and the graphic display during the measurement of time use different display modes, it is easy to judge to which period the pulse rate being displayed belongs. Also, since the pulse rate immediately after or before the external operation to stop the measurement of time is performed and the current pulse rate for a prescribed period following this are displayed simultaneously, it is easy to confirm recovery of the pulse rate.

Termination Of The Recovery Mode

Referring again to FIGS. 14A and 14B, when button switch 114 at the 8 o'clock position is depressed, "PULSE/RESULT" is displayed in dot display area 134 for 1.5 seconds (step ST41), after which the temporal changes in the pulse rate during the marathon are displayed in dot display area 134 (step ST42).

When button switch 114 at the 8 o'clock position is depressed, "PITCH/RESULT" is displayed in dot display area 134 for 1.5 seconds (step ST43), after which the temporal changes in the pitch during the marathon are displayed in dot display area 134 (step ST44).

When button switch 114 at the 8 o'clock position is depressed, "COOLING/DOWN" is displayed in dot display area 134 for 1.5 seconds (step ST45), after which dot display area 134 returns to the graphic display of the temporal changes in the pulse as pulse recovery after crossing the goal (step ST40).

When button switch 116 positioned at the bottom on the front of main unit 10 is depressed after crossing the goal, the message "PROTECT/MEMORY" asking whether or not to save the results is displayed in dot display area 134 (step ST46), and if button switch 117 positioned at the top on the front of main unit 10 is depressed to respond "YES," then "MEMORY" is displayed in dot display area 134 to indicate that the results are being stored (step ST47), and after 2 seconds the display returns to the initial state (step ST31).

The results stored as confirmed data are stored in memory 563 (confirmed data memory means) shown in FIGS. 7 and 8A and 8B, which is capable of storing a plurality of measurement results during a marathon and replaying them later.

When button switch 112 at the 4 o'clock position is depressed after terminating the pulse measuring function, the mode changes to the lap time recall mode (step ST13) as described with reference to FIG. 9.

When button switch 112 at the 4 o'clock position is depressed in this mode, the mode changes to the pulse rate measurement result recall mode (step ST14). In this mode, as well, it is possible to graphically display temporal changes in the pulse rate in dot display area 134.

When button switch 112 at the 4 o'clock position is depressed in this state, the mode returns to the time mode (step ST11).

When returning to this mode, the date is displayed in first segment display area 131 and the current time is displayed in second segment display area 132. Also, "TIME" is displayed in dot display area 134 to indicate return to the time mode, but this display turns off automatically in 2 seconds, and the regular time mode state is established as indicated by arrow P4 (step ST15).

Configuration Of Data Processor For Display

Since only 30 data can be displayed in the time axis direction in dot display area 134 in portable pulse measuring device 1, only 2 minutes worth of pulse rates can be displayed when displaying pulse rate measurement results after completing measurement.

Therefore, as shown in FIGS. 8A and 8B, data processor for display 60 is disposed in display controller 53 for performing display based on data that has been compressed. In this data processor for display 60, the pulse rate data output from pulse data processor 55 and compressed data which has undergone compression are stored in working memory 61. Data compression unit 65 which performs the compression operation on the pulse data stored in working memory 61 and data compression controller 63 which controls the operations performed in this data compression unit 65 are disposed together with working memory 61.

Since two types of compression processing are performed in data processor for display 60, working memory 61 comprises first data memory 611 (compressed data memory means) and second data memory 612 (compressed data memory means). These first and second data memories 611, 612 can each store 30 data for display. Also, data compression unit 65 comprises first data compression unit 66 and second data compression unit 67 for performing two series of compression processing.

Of these, first data compression unit 66 processes the data stored in first data memory 611 at compression factor 1× with respect to time, and each time the number of data stored in first data memory 611 reaches 30, it performs processing based on instructions from data compression controller 63 that doubles the compression factor of the data each time. After second data compression unit 67 compresses the data stored in second data memory 612 at a compression factor of 3× with respect to time, each time the number of data stored in second data memory 612 reaches 30, it performs processing based on instructions from data compression controller 63 that doubles the compression factor of the data each time.

The configurations of first data compression unit 66, second data compression unit 67 and data compression controller 63 for performing this processing are explained by referring to FIG. 22. FIG. 22 is a functional block diagram of the first data compression unit, the second data compression unit and the data compression controller.

As shown in FIG. 22, first data compression unit 66 comprises first 4-second data accumulator 661 which accumulates the pulse data input every 4 seconds, first 4-second data counter 662 which counts the number of data accumulated, and first operation unit 663 which divides the value accumulated in first 4-second data accumulator 661 by the number in first 4-second data counter 662 when the count in first 4-second data counter 662 reaches a prescribed value in order to obtain the average values during that period. The average values sought by first operation unit 663 are sequentially stored in first data memory 661. The number of data stored in first data memory 611 is counted by first compressed data counter 664. During this period, the compression factor of the processing currently being performed is counted by first compression scale counter 665 to be "scale 1," i.e., 1×. First 4-second data counter 662, first compressed data counter 664 and first compression scale counter 665 are monitored by data compression controller 63. When the count value of first compression scale counter 665 is "scale 1," data compression controller 63, assuming the compression factor to be 1×, initiates processing in first operation unit 663 each time first 4-second data counter 662 increments by 1. Therefore, 4-second data is stored as is at this time in first data memory 611.

Of these, when first compression data counter 664 reaches "30," first compression scale counter 665 changes to "scale 2." That is, the compression factor becomes 2×. Here, first averaging processor 666 is disposed in first data compression unit 66, and first averaging processor 666 seeks the 15 averages of adjacent data pairs of the 30 data stored in first data memory 611 based on an instruction from data compression controller 63, after which these 15 averages are stored in first data memory 611 in place of the 30 data stored up to that time. That is, 2× data compression is performed on the 30 data stored in first data memory 611 up to that point. When this processing is performed, first compressed data counter 664 is reset to "15." Following this, when first 4-second data counter 662 becomes "2," data compression controller 63 initiates processing in first operation unit 663, thus causing the average of two 4-second data to be stored in data memory 611.

When first compressed data counter 664 becomes "30" again, first compression scale counter 665 becomes "scale 3." That is, the compression factor becomes 4. First averaging processor 666 seeks the 15 averages of adjacent data pairs of the 30 data stored in first data memory 611 based on an instruction from data compression controller 63, after which these 15 averages are stored in first data memory 611 in place of the 30 data stored up to that time. That is, 2× data compression is performed again on the 30 data stored in first data memory 611 up to that point. When this processing is performed, first compressed data counter 664 is reset to "15." Following this, when first 4-second data counter 662 becomes "4" data compression controller 63 initiates processing in first operation unit 663, thus causing the average of four 4-second data to be stored in data memory 611.

Following this, first 4-second data counter 662 becomes a value that is twice the setting up to that point each time first compressed data counter 664 becomes "30," at which time data compression controller 63 initiates processing by first operation unit 663 wherein the data stored in first data memory 611 are stored as data with a compression factor that is twice the previous compression factor. Also, the 30 data stored in first data memory 611 up to that point become 15 data compressed two times more than they were.

As can be seen from FIG. 22, second data compression unit 67 comprises second 4-second data accumulator 671 which accumulates the pulse data input every 4 seconds, second 4-second data counter 672 which counts the number of data accumulated, and second operation unit 673 which divides the value accumulated in second 4-second data accumulator 671 by the number in second 4-second data counter 672 when the count in second 4-second data counter 672 reaches a prescribed value in order to obtain the average values during that period, and the average values sought by second operation unit 673 are sequentially stored in second data memory 612. Here, as well, the number of data stored in second data memory 612 is counted by second compressed data counter 674. During this period, the compression factor of the processing currently being performed is counted by second compression scale counter 675, and second 4-second data counter 672, second compressed data counter 674 and second compression scale counter 675 are monitored by data compression controller 63. At the beginning, data compression controller 63 first initiates processing in operation unit 673 when second 4-second data counter becomes "3," and therefore the averages of three 4-second data are stored in second data memory 612. That is, second data compression unit 67 begins with a compression factor of 3×. Since the operation of second data compression unit 67 is the same as that of first data compression unit 66 from this point, a detailed explanation is omitted here.

Operation For Data Compression

The operation of first data compression unit 66, second data compression unit 67 and data compression controller 63 configured in this way is explained by referring to FIGS. 23, 23A and 23B. FIGS. 23A and 23B is a flowchart showing the operation performed each time pulse data is input in 4-second intervals.

When pulse data are input in 4-second intervals in step ST101, the data are accumulated in first 4-second data accumulator 661 in step ST102, and the count in first 4-second data counter 662 is incremented by "1" in step ST103.

In step ST104, since the data compression factor is 1× in first data compression unit 66 immediately after the start of measurement, the count in first 4-second data counter 662 is "1" and averages are sought as is in step ST105. In step ST106, first compressed data counter 664 is incremented by "1," after which the average values sought in step ST107 are stored in first data memory 611.

In step ST108, it judged from the count in first compressed data counter 664 whether or not 30 data are stored in first data memory 611, and if 30 data are not stored, then processing proceeds to step ST109.

In step ST109, data are accumulated in second 4-second data accumulator 671, and in step ST110, the count in second 4-second data counter 672 is incremented by "1."

In step ST111, since the data compression factor in second data compression unit 67 is 3× immediately after measurement is started, if the count in second 4-second data counter 672 is not "3," then processing is terminated as is. If the count in second 4-second data counter 672 is "3," however, second compressed data counter 674 is incremented by "1" in step ST113 after seeking the averages in step ST112, after which the sought averages are stored in second data memory 612 in step ST114.

In step ST115, it is judged whether or not 30 data are stored in second data memory 612 from the count of second compressed data counter 674, and if 30 data are not stored, then processing is terminated in step ST116.

When this processing has been repeated for 30 cycles, it is assumed in step ST108 from the count in first compressed data counter 664 that 30 data have been stored in first data memory 611, and first compressed data counter 664 is reset to "15" in step ST117. In step ST118, after the count in first compressed scale counter 665 has been incremented by "1" to "scale 2," first averaging processor 666 seeks 15 averages from the 30 data stored in first data memory 611, and these 15 averages are stored in first data memory 611 in place of the 30 data stored up to that point (step ST119).

In step ST115, if 30 data are stored in second data memory 612 based on the count in second compressed data counter 674, then second compressed data counter 674 is reset to "15" in step ST120. In step ST121, after the count in second compressed scale counter 675 is incremented by "1" to "scale 2," second averaging processor 676 seeks 15 averages from the 30 data stored in second data memory 612, and these 15 data are stored in second data memory 612 in place of the 30 data stored there up that point (step ST122).

As this operation is repeated, as shown in TABLE 1, the counts in first and second compression scale counters 665, 657 are increased to "scale 1," "scale 2," etc., as time elapses. Each time, the number of data averaged by first operation unit 663 are doubled from 1 to 2, 4, 8, 16, 32, etc., and the number of data averaged by second operation unit 673 are doubled from 3 to 6, 12, 24, etc.

In this way, by performing data compression as time elapses, the number of data stored in first and second data memories 611, 612 decreases, but display switching controller 530 can graphically display temporal changes in the pulse rate in dot display area 134 of liquid crystal display

TABLE 1

| | Time elapsed (minutes) | 2 | 4 | 6 | 8 | 12 | 16 | 24 | 32 | 48 | 64 | 96 |
|---|---|---|---|---|---|---|---|---|---|---|---|---|
| First data compression unit | Compression scale | 1 | 2 | 3 | | 4 | | 5 | | 6 | | |
| | Compression factor | 1 | 2 | | 4 | | 8 | | 16 | | 32 | |
| | Number of averaged data | 1 | 2 | | 4 | | 8 | | 16 | | 32 | |
| | Time (minutes) represented by 30 data | 1 | | | 4 | | 8 | | 16 | | 32 | 64 |
| Second data compression unit | Compression scale | | | 1 | | 2 | | 3 | | 4 | | 5 |
| | Compression factor | | | | | 3 | | 6 | | 12 | 24 | 48 |
| | Number of averaged data | | | | | 3 | | 6 | | 12 | 24 | 48 |
| | Time (minutes) represented by 30 data | | | | | 6 | | 12 | | 24 | 48 | 96 |

As a result, the compression factor in first data compression unit 66 is doubled each time from 1× to 2×, 4×, 8×, 16×, 32×, etc. The compression factor in second data compression unit 67 is doubled each time from 3× to 6×, 12×, 24×, etc. For this reason, the time in minutes represented by the 30 data stored in first data memory 611 is extended to 2, 4, 8, 16, 32, 64, etc. The time in minutes represented by the 30 data stored in second data memory 612 is extended to 6, 12, 24, 48, 96, etc.

Therefore, display switching controller 530 shown in FIGS. 7, 8, 8A and 8B is capable of graphically displaying temporal changes in the pulse rate in dot display area 134 based on compressed data stored in the data memory of first and second data memories 611, 612 wherein the greater number of data are stored.

If, however, data compression of the data is simply performed at a fixed compression factor of 2, for example, then the display of 30 data would change to the display of 15 data, thus decreasing the amount of information displayed. For the purpose of solving this problem, as described by referring to FIGS. 8A to 10 and TABLE 1, data that has been compressed at differing compression factors are stored as compressed data in first and second data memories 611, 612, and when there is an instruction to display pulse rate measurement results upon completion of measurement, display switching controller 530 graphically displays temporal changes in the pulse rate in dot display area 134 of liquid crystal display device 13 based on the compressed data stored in the data memory of first and second data memories 611, 612 with the greater number of data.

That is, in TABLE 1, when four minutes has elapsed from the start of measurement, first data memory 611 undergoes compression processing, and therefore the number of data stored in first data memory 611 becomes 15, but since second data memory 612 does not undergo data compression until 6 minutes has elapsed, it has 20 data after 4 minutes has elapsed. Display switching controller 530, as shown in FIG. 24, graphically displays temporal changes in the pulse in dot display area 134 based on the 20 data stored in second data memory 612. Following this, when the number of data stored in first or second data memory 611, 612 reaches 30, the compression factor of the compressed data stored up to that point is increased by one rank or order of magnitude and the data is recompressed, and therefore it is judged which data memory contains the greater number of compressed data and display is performed based on the compressed data stored in the data memory with the greater number of data.

device 13 based on the compressed data stored in the data memory of first and second data memories 611, 612 with the greater number of data. Therefore, even when the number of data stored in first or second data memory 611, 612 reaches 30, since the compression factor of the compressed data stored up to that point is increased by one rank and the data are recompressed to 15 data and display is performed based on the compressed data stored in the data memory with the greater number of data, the measurement results can be correctly displayed regardless of the length of the measurement time without having to increased the size of dot display area 134.

Further, since the data compression factor in first data compression unit 66 changes from 1× to 2×, 4×, 8×, etc., and the compression factor in second data compression unit 67 changes from 3× to 12×, 24×, etc., the compression factor changes almost continuously with the passage of time. For this reason, even though data compression is performed, temporal changes in the measurement results vary only slightly and it is possible to see temporal changes in the measurement results any time.

When storing the measurement results from a marathon in memory 563 upon completion of the marathon, it is possible to store together with the time data only the compressed data stored in the data memory of first and second data memories 611, 612 with the greater number of data. Here, the area used in memory 563 is 10 measurements of confirmed data. Therefore, the measurement results stored up to that time in memory 563 are specified and deleted, and the new confirmed data are stored there.

In the above embodiment, compression processing was performed using two systems, but compression processing can be performed using three or more systems.

Different Display Method For Pulse Rate Using Data Compression

When the measured pulse rate is displayed again after terminating measurement in the above embodiment, as much information as possible is displayed using compressed data, but by using compressed data for display during time measurement, it is possible to display as many temporal changes in the pulse rate as possible from when time measurement was started up to the present.

That is, data compressed at differing compression rates is stored in first and second data memories 611, 612, and display switching controller 530 graphically displays temporal changes in the pulse rate in dot display area 134 of liquid crystal display device 13 based on compressed data stored in the data memory of first and second data memories 611, 612 with the greater number of data.

That is, in TABLE 1 the pulse (difference between pulse rate and reference pulse rate) is displayed based on data stored in first data memory 611 from the time measurement starts until 2 minutes has elapsed. Also, when first data memory 611 undergoes compression after 4 minutes has elapsed, the number of data stored in first data memory 611 becomes 15, but since second data memory 612 does not undergo data compression until 6 minutes has elapsed, it has 20 data after 4 minutes has elapsed. Therefore, display switching controller 530, as shown in FIG. 24, graphically displays temporal changes in the pulse in dot display area 134 based on the 20 data stored in second data memory 612.

Following this, when the number of data stored in first or second data memory 611, 612 reaches 30, the compression factor of the compressed data stored up to that point is increased by one rank and the data is recompressed, at which time it is judged which data memory contains the greater number of compressed data and display is performed based on the compressed data stored in the data memory with the greater number of data.

Other Operations

Again, in FIG. 7, switch mechanism 500 for detecting the presence of a battery is inserted between IC 56 and line 57 electrically connected to the positive electrode of battery 59 and the terminals of capacitance elements 528, 558, and this switch mechanism 500 opens and closes with the insertion and removal of battery 59.

That is, in mode switching unit 564 of IC 56, switch mechanism 500 closes when battery 59 is removed in order to replace it, and when the prescribed signal (terminal voltage of capacitance element 528) is input from line 57 via switch mechanism 500, an operation is performed that switches from the normal mode to a power-saving mode that forcibly stops some of the operations performed in main unit 10. In the power-saving mode, mode switching unit 564 first stops the supply of power to voltage booster circuit 580 for generating the notification sound, the output of the clock signal to IC 50, and the supply of power to voltage booster circuit 541 for liquid crystal display, and in addition to this, drive circuit 562 for liquid crystal display completely stops display by making the common voltage and the segment voltages of liquid crystal display device 13 the same potential. When this power-saving mode is active, the power required to continue the clock operation and to backup memories 563, 501 is supplied from capacitance elements 528, 558. Therefore, since the clock function continues to operate even after battery 59 has been removed, it is not necessary to reset the time after replacing battery 59. Also, the data stored in memories 563, 501 is not lost.

When battery 59 is inserted, switch mechanism 500 goes to an open state, which stops the input of the signal. However, no power is supplied from battery 59 until the back cover is attached. Since voltage detector 543 monitors this condition, mode switching unit 564 resets from the power-saving mode to the normal mode only when back cover 118 is attached after inserting battery 59 and battery 59 begins supplying power. In addition, mode switching unit 564 immediately displays the voltage detected between the terminals of newly inserted battery 59 by voltage detector 543.

While the invention has been described in conjunction with several specific embodiments, it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

| REFERENCE NUMERALS | |
|---|---|
| 1 | portable pulse measuring device |
| 5 | control unit |
| 10 | main unit |
| 12 | wrist band |
| 13 | liquid crystal display device (display device) |
| 30 | sensor unit (pulse signal detection member) |
| 31 | LED |
| 32 | phototransistor |
| 40 | band for securing sensor |
| 53 | display controller |
| 55 | pulse data processor |
| 70 | connector member |
| 80 | connector piece |
| 111–117 | button switches (switches for external operation) |
| 131 | first segment display area |
| 132 | second segment display area |
| 133 | third segment display area |
| 134 | dot display area |
| 530 | display switching controller |
| 531 | waveform data converter |
| 532 | sweep display processor |
| 564 | mode switching unit |

What is claimed is:

1. Display method in a portable pulse measuring device comprising the steps of:
   (a) measuring a pulse rate;
   (b) switching a graphic display mode between a first measurement period until the pulse rate measured in step (a) reaches a reference pulse rate after measurement of the pulse rate has started and a second measurement period after the pulse rate has reached the reference pulse rate; and
   (c) graphically displaying time varying changes in the measured pulse rate in a first graphical mode during the first measurement period and a second graphical mode during the second measurement period on a display device.

2. A display method in a portable pulse measuring device of claim 1, further comprising the steps of:
   selecting among an input mode for inputting first information and one of plural display modes for displaying second information by an external operation;
   displaying one of the first and second information of the selected mode; and
   terminating the display of information of the selected mode automatically after a prescribed time has elapsed.

3. A display method in a portable pulse measuring device of claim 2, further comprising the steps of:
   displaying time information in a segment display area;
   graphically displaying in a dot display area information of the selected mode; and
   automatically terminating display of the mode information after a prescribed time.

4. Display method in a portable pulse measuring device comprising the steps of:
   (a) measuring a pulse rate;
   (b) switching a graphic display mode between a first measurement period until the pulse rate measured in step (a) reaches a reference pulse rate after measurement of the pulse rate has started and a second measurement period after the pulse rate has reached the reference pulse rate; and (c) graphically displaying time varying changes in the measured pulse rate on a display device, wherein step (c) further comprises displaying a bar graph in the first measurement period that extends according to the absolute value of the measured pulse rate; and displaying a bar graph in the second measurement period, that extends in at least one of a positive direction and a negative direction at each time interval according to a difference between the measured pulse rate and the reference pulse rate.

5. A display method in a portable pulse measuring device of claim 4, further comprising the steps of:

switching the graphic display based on an external operation between display of temporal changes in the pulse rate and display of temporal changes in a pitch based on a measured results of an acceleration sensor; and displaying temporal changes in the pitch in a segmented graph plotted at each time period corresponding to an absolute value of the pitch.

6. Display method in a portable pulse measuring device comprising the steps of:

(a) measuring a pulse rate;

(b) switching a graphic display mode between a first measurement period until the pulse rate measured in step (a) reaches a reference pulse rate after measurement of the pulse rate has started and a second measurement period after the pulse rate has reached the reference pulse rate;

(c) graphically displaying time varying changes in the measured pulse rate in a first mode during the first measurement period and a second mode during the second measurement period on a display device;

(d) measuring time contemporaneously with step (a);

(e) performing an external operation that stops measurement of time of step (d);

(f) measuring of the pulse rate contemporaneously with step (e); and (g) graphically displaying time varying changes in the measured pulse rate in a mode other than the second mode while continuing to measure the pulse rate for a prescribed period.

7. A display method in a portable pulse measuring device of claim 6, wherein the pulse rate in one of immediately after and immediately before step (d) is displayed contemporaneously with a current pulse rate displayed for the prescribed time period in the display device.

8. Display method in a portable pulse measuring device comprising the steps of:

(a) measuring a pulse rate;

(b) switching a graphic display mode between a first measurement period until the pulse rate measured in step (a) reaches a reference pulse rate after measurement of the pulse rate has started and a second measurement period after the pulse rate has reached the reference pulse rate;

(c) graphically displaying time varying changes in the measured pulse rate on a display device; and (d) switching the graphic display mode based on an external operation between display of time varying changes in the pulse rate and display of time varying changes in a pitch based on measured results of an acceleration sensor; and wherein the graphic display mode for time varying changes in the pulse rate in the first and second measurement periods is different from the graphic display mode for time varying changes in the pitch.

9. Display method in a portable pulse measuring device comprising the steps of:

(a) measuring a pulse rate;

(b) switching a graphic display mode between a first measurement period until the pulse rate measured in step (a) reaches a reference pulse rate after measurement of the pulse rate has started and a second measurement period after the pulse rate has reached the reference pulse rate;

(c) graphically displaying time varying changes in the measured pulse rate on a display device;

(d) graphically displaying a pulse signal, from the time the mode is changed to the pulse rate measurement mode based on an external operation, until an external operation is performed to start the measurement of time; and graphically displaying the pulse rate after an external operation is performed to start the measurement of time.

10. A display method in a portable pulse measuring device of claim 9, further comprising the steps:

displaying the pulse rate from a time display mode is changed to the pulse rate measurement mode based on an external operation, until processing that determines the pulse rate is enabled; and displaying the pulse rate after processing that determines the pulse rate is enabled, until the external operation that starts the measurement of time is performed.

11. A display method in a portable pulse measuring device of claim 9, further comprising the steps of:

amplifying the pulse signal until a prescribed amplitude;

graphically displaying the pulse signal; and displaying an amplification level.

12. A display method in a portable pulse measuring device of claim 9, further comprising the step of:

consuming a first amount of power during a first power mode and a second amount of power during a second mode, wherein the second amount of power is greater than the first amount of power; and switching the display when graphically displaying the pulse signal, to newly measured pulse signals when consuming the first amount of power, but consuming the second amount of power fixing the display at the pulse signal that was being displayed until consuming the second amount of power is terminated.

13. A display method in a portable measuring device of claim 12, wherein consumption of the second amount of power occurs when a backlight is illuminated or when an alarm in initiated.

14. Display method in a portable pulse measuring device comprising the steps of:

(a) measuring a pulse rate;

(b) switching a graphic display mode between a first measurement period until the pulse rate measured in step (a) reaches a reference pulse rate after measurement of the pulse rate has started and a second measurement period after the pulse rate has reached the reference pulse rate;

(c) graphically displaying time varying changes in the measured pulse rate in a first mode during the first measurement period and a second mode during the second measurement period on a display device;

(d) compressing data by means of a plurality of data compression means with respect to time of at least an order of magnitude of two of the measurement results of the pulse rate measured at each fixed time.

(e) recompressing data stored in compressed data memory means at a compression factor increased by an order of magnitude of one when a number of data stored in the compressed data memory means reaches a value set according to the compression by means of a data compression control means that controls the data compression means;

(f) storing subsequent data in the compressed data memory means as compressed data compressed at a compression factor increased by an order of magnitude of one; and (g) graphically displaying time varying changes in the pulse on the display device based on the compressed data stored in the compressed data memory means.

15. A display method in a portable pulse measuring device of claim 14, further comprising the steps of:

(h) doubling the compression factor after each time the number of data stored in the corresponding compressed data memory means reaches a set value after data compression of the measurement results is performed at a one times compression factor;

doubling the compression factor after each time the number of data stored in the corresponding compressed data memory means reaches a set value after data compression of the measurement results is performed at a three times compression factor; and graphically displaying time varying changes in the pulse on the display device based on the results of data processing by these two data compression means.

16. A display method in a portable pulse measuring device of claim 14, further comprising the step of graphically displaying time varying changes in the pulse rate after completion of measurement based on the compressed data stored in the compressed data memory means of the plurality of compressed data memory means wherein the greatest number of data are stored.

17. A display method in a portable pulse measuring device of claim 14, further comprising the steps of:

judging which one of the compressed data memory means has a greatest number of data stored when the number of data stored in the compressed data memory means reaches the set value and the compressed data stored are recompressed at a compression factor one an order of magnitude higher; and switching the graphic display of time varying changes in the pulse rate based on the compressed data stored in the compressed data memory means with the greatest number of data.

18. A display method in a portable pulse measuring device of claim 14 further comprising the steps of:

storing based on an external operation, after completion of measurement, the compressed data stored in the compressed data memory means of the compressed data memory means with the greatest number of data; and graphically redisplaying the time varying changes in the pulse rate based on said compressed data.

* * * * *